United States Patent [19]

Dow et al.

[11] Patent Number: 5,843,972

[45] Date of Patent: Dec. 1, 1998

[54] HETEROCYCLIC β-ADRENERGIC AGONISTS

[75] Inventors: Robert L. Dow; Stephen W. Wright, both of Groton, Conn.

[73] Assignee: Pfizer Inc., New York, N.Y.

[21] Appl. No.: 827,289

[22] Filed: Mar. 28, 1997

Related U.S. Application Data

[60] Provisional application No. 60/015,216 Apr. 9, 1996.

[51] Int. Cl.$^6$ .................... A61K 31/38; A61K 31/425; C07D 307/02; C07D 277/60

[52] U.S. Cl. .................. 514/367; 514/443; 514/444; 514/469; 514/255; 514/256; 514/258; 514/365; 514/372; 514/373; 514/374; 514/375; 514/415; 544/253; 548/152; 548/217; 548/237; 549/49; 549/58; 549/491; 549/492

[58] Field of Search ............... 544/253; 548/152, 548/217, 237; 549/49, 58, 491, 492, 495; 514/443, 444, 469, 255, 256, 258, 365, 367, 372, 373, 374, 375, 415

[56] References Cited

U.S. PATENT DOCUMENTS

| | | | |
|---|---|---|---|
| 3,644,353 | 2/1972 | Lunts et al. | 260/247.5 R |
| 3,705,233 | 12/1972 | Lunts et al. | 424/45 |
| 4,309,443 | 1/1982 | Smith et al. | 424/319 |
| 4,341,793 | 7/1982 | Ferries | 424/285 |
| 4,385,066 | 5/1983 | Ainsworth et al. | 424/309 |
| 4,432,993 | 2/1984 | Ferries | 424/285 |
| 5,627,200 | 5/1997 | Kreutter et al. | 514/365 |

*Primary Examiner*—S. Mark Clardy
*Assistant Examiner*—Sabiha N. Qazi
*Attorney, Agent, or Firm*—Peter C. Richardson; Gregg C. Benson; Robert T. Ronau

[57] ABSTRACT

The present invention relates to certain compounds of the formula (I) the racemic-enantiomeric mixtures and optical isomers of said compounds and the pharmaceutically acceptable salts or prodrugs thereof, depicted below, which are β-adrenergic receptor agonists and accordingly have utility as, inter alia, hypoglycemic and antiobesity agents. More specifically, the compounds of the instant invention are selective agonists of $\beta_3$-adrenergic receptor. The invention also relates to methods of use for the compounds and to pharmaceutical compositions containing them. The compounds of the present invention also possess utility for increasing lean meat deposition and/or improving the lean meat to fat ratio in animals, e.g., ungulate animals, companion animals and poultry. The compounds have the formula

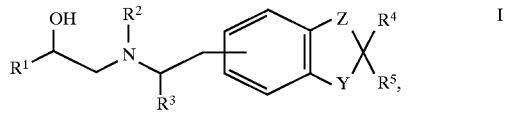

wherein $R^1$, $R^2$, $R^3$, $R^4$, $R^5$, Y and Z are as defined in the specification.

15 Claims, No Drawings

HETEROCYCLIC β-ADRENERGIC AGONISTS

CROSS REFERENCE TO RELATED APPLICATIONS

This application is a nonprovisional application claiming benefit of provisional application Ser. No. 60/015,216, filed Apr. 9, 1996.

BACKGROUND OF THE INVENTION

The present invention relates to certain compounds of the formula (I) depicted below, which are β-adrenergic receptor agonists and accordingly have utility as, inter alia, hypoglycemic and antiobesity agents. More specifically, the compounds of the instant invention are selective agonists of the $\beta_3$-adrenergic receptor. The invention also relates to methods of use for the compounds and to pharmaceutical compositions containing them. The compounds of the present invention also possess utility for increasing lean meat deposition and/or improving the lean meat to fat ratio in animals, e.g. ungulate animals, companion animals and poultry.

The compounds of this invention further possess utility in the treatment of intestinal motility disorders, depression, prostate disease, dyslipidemia, and airway inflammatory disorders such as asthma and obstructive lung disease.

The disease diabetes mellitus is characterized by metabolic defects in production and utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The compounds of the present invention and the pharmaceutically acceptable salts thereof effectively lower blood glucose levels when administered to mammals with hyperglycemia or diabetes.

The compounds of the present invention also reduce body weight or decrease weight gain when administered to mammals and poultry. The ability of these compounds to affect weight gain is due to activation of $\beta_3$-adrenergic receptors which stimulate the metabolism of adipose tissue.

β-Adrenergic receptors have been categorized into $\beta_1$, $\beta_2$ and $\beta_3$-subtypes. Agonists of β-receptors promote the activation of adenyl cyclase. Activation of $\beta_1$-receptors invokes increases in heart rate while activation of $\beta_2$-receptors induces relaxation of skeletal muscle tissue which produces a drop in blood pressure and the onset of smooth muscle tremors. Activation of $\beta_3$-receptors is known to stimulate lipolysis (the breakdown of adipose tissue triglycerides to glycerol and free fatty acids) and metabolic rate (energy expenditure), and thereby promote the loss of fat mass. Compounds that stimulate $\beta_3$-receptors are therefore useful as anti-obesity agents, and can also be used to increase the content of lean meat in animals and poultry. In addition, compounds which are $\beta_3$-receptor agonists have hypoglycemic or anti-diabetic activity, but the mechanism of this effect is uncertain.

Until recently $\beta_3$-adrenergic receptors were thought to be found predominantly in adipose tissue. $\beta_3$-receptors are now known to be located in such diverse tissues as the intestine (*J. Clin. Invest.*, 91, 344 (1993)) and the brain (*Eur. J. Pharm.*, 219,193 (1992)). Stimulation of the $\beta_3$-receptor has been demonstrated to cause relaxation of smooth muscle in colon, trachea and bronchi. *Life Sciences*, 44(19), 1411 (1989); *Br. J. Pharm.*, 112, 55 (1994); *Br. J. Pharmacol.*, 110, 1311 (1993). For example, stimulation of $\beta_3$-receptors has been found to induce relaxation of histamine-contracted guinea pig ileum, *J.Pharm. Exp. Ther.*, 260, 1,192 (1992).

The $\beta_3$-receptor is also expressed in human prostate. Because stimulation of the $\beta_3$-receptor causes relaxation of smooth muscles that have been shown to express the $\beta_3$-receptor (e.g. intestine), one skilled in the art would predict relaxation of prostate smooth muscle. Therefore, $\beta_3$-agonists are useful for the treatment or prevention of prostate disease, such as benign prostatic hypertrophy.

U.S. Pat. No. 5,061,727 concerns certain substituted 5-(2-((2-aryl-2-hydroxyethyl)amino)-propyl)-1,3-benzodioxoles which are disclosed to possess anti-diabetic and/or anti-hyperglycemic and/or anti-obesity properties.

European Patent publication 516,349, published Dec. 2, 1992, refers to certain 2-hydroxyphenethyl amines which possess antiobesity, hypoglycemic and related utilities.

U.S. Pat. No. 4,358,455 is concerned with certain heterocyclic compounds of the formula Het—CHOH—CH$_2$—NH-aralkyl, useful for treating glaucoma and cardiovascular disorders.

U.S. Pat. No. 5,030,640 concerns certain a-heterocyclic ethanol amino alkyl indoles, useful as growth promoters, bronchodilators, antidepressants and antiobesity agents.

U.S. Pat. No. 5,019,578 concerns certain a-heterocyclic ethanol amines useful as growth promoters.

SUMMARY OF THE INVENTION

This invention relates to compounds having the formula I

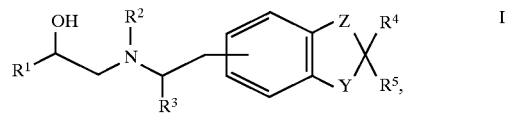

the racemic-enantiomeric mixtures and optical isomers of said compounds or a pharmaceutically acceptable salt or prodrug thereof,
wherein
$R^1$ is an optionally substituted phenyl, optionally substituted phenoxyalkyl having 1 to 4 carbons in the alkoxy portion, optionally substituted pyridinyl, optionally substituted pyrimidyl, optionally substituted thiazolyl or optionally substituted oxazolyl;
where the optionally substituted moieties of $R^1$ are optionally substituted with one to three substituents, each substituent is independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, $(C_1-C_4)$alkoxycarbonyl, $(C_1-C_4)$thioalkyl, sulfonyl, sulfinyl, amino, —NH—CO—$(CH_2)_a$-(phenyl), —NH—CO—$(C_1-C_{10})$alkyl, —NH—SO$_2$—$(CH_2)_a$-(phenyl) and —NH—SO$_2$—$(C_1-C_{10})$alkyl;
$R^2$ is hydrogen or $(C_1-C_6)$alkyl;

$R^3$ is hydrogen or $(C_1-C_6)$alkyl;

$R^4$ and $R^5$ are each independently selected from the group consisting of hydrogen, $-CO_2H$, $-CO_2R^6$, $-CO_2NR^6R^6$, $-CHO$, $-COR^6$, $-CH_2OH$, $-CH_2OCH_2CO_2R^6$ and $-CH_2OCH_2CH_2OR^6$;

$R^6$ for each occurrence is independently selected from the group consisting of hydrogen and $(C_1-C_4)$alkyl;

Y is oxygen, sulfur or $NR^7$;

Z is $-(CH_2)_n-$;

n is 1 or 2;

$R^7$ is hydrogen, $(C_1-C_{10})$alkyl, $(C_1-C_{10})$alkenyl, $-(CH_2)_a$-(optionally substituted phenyl), $-(CH_2)_a$-(optionally substituted pyridinyl), $-CO-(CH_2)_a$-(optionally substituted phenyl), $-CO-(C_1-C_{10})$alkyl, $-SO_2-(CH_2)_a$-(optionally substituted phenyl) or $-SO_2-(C_1-C_{10})$alkyl;

where the optionally substituted moieties in the definition of $R^7$ are optionally substituted with one to three substituents, each independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, $(C_1-C_4)$alkoxycarbonyl, $(C_1-C_4)$thioalkyl, sulfonyl, sulfinyl, amino, $-NH-CO-(CH_2)_a$-(phenyl), $-NH-CO-(C_1-C_{10})$alkyl, $-NH-SO_2-(CH_2)_a$-(phenyl) and $-NH-SO_2-(C_1-C_{10})$alkyl;

a is 0, 1, 2, 3 or 4 provided that $R^4$ and $R^5$ are not both hydrogen at the same time.

The present invention also relates to pharmaceutical compositions, useful for treating a condition, disease, or disorder in a mammal or poultry, including any of the conditions, diseases and/or disorders disclosed herein, comprising an amount of a compound of formula I, or a prodrug thereof, or a pharmaceutically acceptable salt of said compound or prodrug, as defined hereinabove, effective in treating such condition, disease, or disorder, and a pharmaceutically acceptable carrier. Specific conditions, diseases, and/or disorders which are treatable with such compositions include diabetes, hyperglycemia, obesity, intestinal motility disorders, airway inflammatory disorders, depression, prostate disease, and dyslipidemia.

This invention also relates to a method of selectively activating a $\beta_3$-adrenergic receptor in a mammal or poultry, comprising administering to a mammal or poultry in need of such activation an effective amount of a compound of formula (I) or a prodrug thereof, or a pharmaceutically acceptable salt of said compound or prodrug, as defined hereinabove.

Preferred compounds, designated 'Group A', are those compounds of formula (I), as defined hereinabove, where $R^1$ is optionally substituted phenyl; $R^3$ is $(C_1-C_6)$alkyl; $R^4$ is hydrogen or $-CO_2R^6$; and $R^5$ is $-CO_2R^6$ and the other substituents are as defined in the foregoing definition of formula (I).

Compounds which are preferred among the 'Group A' compounds, designated 'Group B', are those compounds of Group A further defined in that the optionally substituted phenyl of $R^1$ is optionally substituted with a chloro, fluoro, iodo or bromo.

Compounds which are preferred among the 'Group B' compounds, designated 'Group C', are those compounds of Group B further defined in that $R^1$ is

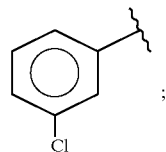

$R^2$ is hydrogen; and the OH in formula I has the

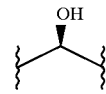

configuration.

Compounds which are preferred among the 'Group C' compounds, designated 'Group D', are those compounds of Group C further defined in that $R^3$ is methyl and Y is $NR^7$.

Compounds which are preferred among the 'Group D' compounds, designated 'Group E', are those compounds of Group D further defined in that $R^4$ and $R^5$ are each $-CO_2CH_3$; Z is $-CH_2-$; and $R^7$ is $-SO_2$-phenyl, $-CO$-phenyl or $-COCH_3$.

Compounds which are also preferred among the 'Group D' compounds, designated 'Group F', are those compounds of Group D further defined in that $R^4$ is hydrogen, $R^5$ is $-CO_2CH_3$; Z is $-CH_2-$; and $R^7$ is $-CO$-phenyl.

Another group of compounds which are preferred among the 'Group D' compounds, designated 'Group G', are those compounds of Group D further defined in that $R^4$ and $R^5$ are each $-CO_2CH_3$; Z is $-CH_2-$; and $R^7$ is benzyl or $-CO$-benzyl.

Yet another group of compounds which are preferred among the 'Group D' compounds, designated 'Group H', are those compounds of Group D further defined in that $R^4$ and $R^5$ are each $-CO_2CH_2CH_3$; $R^7$ is benzyl; and Z is $-CH_2-CH_2-$.

Still another group of compounds which are preferred among the 'Group D' compounds, designated 'Group I', are those compounds of Group D further defined in that $R^4$ is hydrogen; $R^5$ is $-CO_2CH_3$; Z is $-CH_2-$; and $R^7$ is benzyl.

Further still another group of compounds which are preferred among the 'Group D' compounds, designated 'Group J', are those compounds of Group D further defined in that $R^4$ and $R^5$ are each $-CO_2CH_3$; Z is $-CH_2-$; and $R^7$ is hydrogen, methyl or ethyl.

Compounds which are preferred among the 'Group C' compounds, designated 'Group K', are those compounds of Group C further defined in that $R^3$ is methyl; Y is O; and $R^4$ and $R^5$ are each $-CO_2CH_2CH_3$.

Salt forms of the above compounds are also preferred.

The present invention also relates to a process for the preparation of a compound having the formula (M)

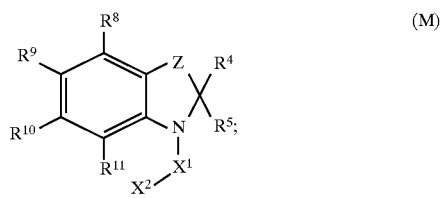

wherein $R^8$, $R^9$, $R^{10}$ and $R^{11}$ are each independently selected from the group consisting of hydrogen, halo, nitro, $(C_1-C_6)$alkoxy, $(C_1-C_6)$thioalkoxy, $-(C_1-C_5)$alkyl$-CHO$, CHO, alkoxyalkyl having 1–6 carbons in the alkoxy portion and 1–6 carbons in the alkyl portion, nitrile, alkylcarbonylalkyl having 1–6 carbons in each of the alkyl portions, $(C_1-C_6)$ alkyl, trifluoromethyl, —$CHF_2$, —$CH_2F$ and optionally substituted phenyl;

or $R^8$ and $R^9$, or $R^9$ and $R^{10}$, or $R^{10}$ and $R^{11}$ are taken together and form a fused phenyl ring;

$R^4$ and $R^5$ are each independently selected from the group consisting of hydrogen, —$CO_2H$, —$CO_2R^6$, —$CO_2NR^6R^6$, —CHO, —$COR^6$, —$CH_2OH$, —$CH_2OCH_2CO_2R^6$ and —$CH_2OCH_2CH_2OR^6$;

$R^6$ for each occurrence is independently selected from the group consisting of hydrogen and $(C_1-C_4)$alkyl;

Z is —$CH_2$- or —$CH_2$—$CH_2$—;

$X^1$ is C=O or $SO_2$; and $X^2$ is $CF_3$, $CCl_3$, $(C_1-C_6)$alkyl, optionally substituted phenyl, $(C_1-C_4)$perfluoro-alkyl, amide or sulfonamide; where the optionally substituted phenyl is optionally substituted with one to three substituents, each independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, alkoxycarbonyl, $(C_1-C_4)$thioalkyl, sulfonyl, sulfinyl, amino, —NH—CO—$(CH_2)_a$-(phenyl), —NH—CO—$(C_1-C_{10})$alkyl, —NH—$SO_2$—$(CH_2)_a$-(phenyl) and —NH—$SO_2$—$(C_1-C_{10})$alkyl; comprising reacting a compound of the formula (MX)

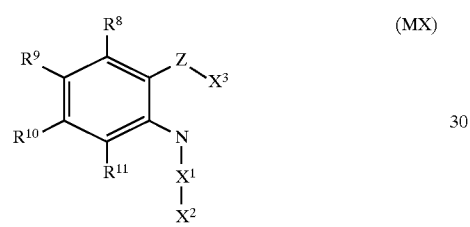

(MX)

wherein $R^8$, $R^9$, $R^{10}$, $R^{11}$, $X^1$, $x^2$ and Z are as defined immediately hereinabove for the compound of formula (M) and where $X^3$ is Br, Cl, I, mesyl, tosyl or trifyl;

(X)

with a compound of formula (X),
where $R^4$ and $R^5$ are as defined immediately hereinabove for the compound of formula (M);
in the presence of a non-nucleophilic base. A preferred process of the immediately foregoing process is a process wherein the temperature range for reacting said compound of formula (MX) in the presence of said non-nucleophilic base is conducted at about –30° C. to 50° C. An even more preferred process of the immediately foregoing process is wherein the temperature range is at about –10° C. to 20° C.

Preferred is a process for preparing a compound of formula (M) as defined hereinabove, where $R^9$ is halo.

A preferred process of the immediately foregoing process is when $R^8$, $R^{10}$ and $R^{11}$ are each hydrogen.

A preferred process of the immediately foregoing process is when $X^1$ is C=O.

A preferred process of the immediately foregoing process is when $X^2$ is $CF_3$.

A preferred process of the immediately foregoing process is when the non-nucleophilic base is sodium hydride, potassium t-butoxide or potassium carbonate.

This invention also relates to intermediate compounds which are useful in the synthesis of compounds of formula (I) as defined herein. The intermediate compounds provided in the present invention are as follows:

(i) a compound of the formula MXI

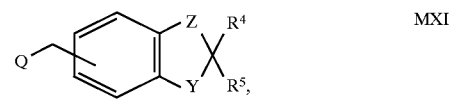

MXI wherein Q is $R^3$—C(=O)— or $R^3$—CH($NH_2$)—; $R^3$ is hydrogen or $(C_1-C_6)$alkyl; $R^4$ and $R^5$ are each independently selected from the group consisting of hydrogen, $CO_2H$, $CO_2R^6$, $CONR^6R^6$, CHO, $COR^6$, $CH_2OH$, $CH_2OCH_2CO_2R^6$ and $CH_2OCH_2CH_2OR^6$ provided that $R^4$ and $R^5$ may not both simultaneously be hydrogen; $R^6$ for each occurence is independently hydrogen or $(C_1-C_4)$alkyl; Y is O, S, or $NR^7$; $R^7$ is selected from the group consisting of hydrogen, $(C_1-C_{10})$alkyl, $(C_1-C_{10})$alkenyl, —$(CH_2)_a$-(optionally substituted phenyl), —$(CH_2)_a$- (optionally substituted pyridinyl), —CO—$(CH_2)_a$-(optionally substituted phenyl), —CO—$(C_1-C_{10})$alkyl, —$SO_2$—$(CH_2)_a$-(optionally substituted phenyl) and —$SO_2$—$(C_1-C_{10})$alkyl; a is 0, 1, 2, 3, or 4; and Z is —$CH_2$— or —$CH_2CH_2$—; where the optionally substituted phenyl and optionally substituted pyridinyl are each optionally substituted with one to three substituents, each independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, alkoxycarbonyl, $(C_1-C_4)$thioalkyl, sulfonyl, sulfinyl, amino, —NH—CO—$(CH_2)_a$-(phenyl), —NH—CO—$(C_1-C_{10})$alkyl, —NH—$SO_2$—$(CH_2)_a$-(phenyl) and —NH—$SO_2$—$(C_1-C_{10})$alkyl;

(ii) a compound of formula MXII

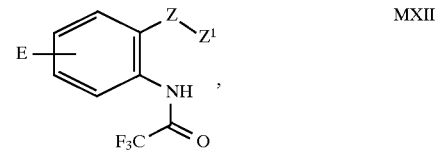

MXII wherein E is iodo, bromo, chloro, fluoro, or hydrogen; Z is —$CH_2$— or —$CH_2CH_2$—; and $Z^1$ is OH or Br;

(iii) a compound of formula XI

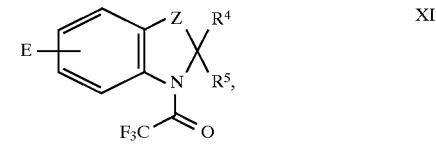

XI wherein E is iodo, bromo, chloro, fluoro or hydrogen; $R^4$ and $R^5$ are each independently selected from the group consisting of hydrogen, $CO_2H$, $CO_2R^6$, $CONR^6R^6$, CHO, $COR^6$, $CH_2OH$, $CH_2OCH_2CO_2R^6$ and $CH_2OCH_2CH_2OR^6$ provided that $R^4$ and R5 may not both simultaneously be hydrogen; $R^6$ for each occurence is independently hydrogen or $(C_1-C_4)$alkyl; and Z is —$CH_2$— or —$CH_2CH_2$—;

(iv) a compound of formula XVI

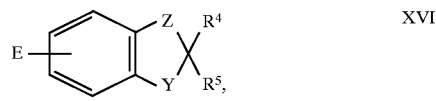

XVI wherein E is iodo, bromo, chloro, fluoro or hydrogen; $R^4$ and $R^5$ are each independently selected from the group consisting of hydrogen, $CO_2H$, $CO_2R^6$, CONR$^6$R$^6$, CHO, COR$^6$, CH$_2$OH, CH$_2$OCH$_2$CO$_2$R$^6$ and CH$_2$OCH$_2$CH$_2$OR$^6$ provided that R$^4$ and R$^5$ may not both simultaneously be hydrogen; R$^6$ for each occurence is independently hydrogen or (C$_1$–C$_4$)alkyl; Y is O, S, or NR$^7$; R$^7$ is selected from the group consisting of hydrogen, (C$_1$–C$_{10}$)alkyl, (C$_1$–C$_{10}$)alkenyl, —(CH$_2$)$_a$-(optionally substituted phenyl), —(CH$_2$)$_a$-(optionally substituted pyridinyl), —CO—(CH$_2$)$_a$-(optionally substituted phenyl), —CO—(C$_1$–C$_{10}$)alkyl, —SO$_2$—(CH$_2$)$_a$-(optionally substituted phenyl) and —SO$_2$—(C$_1$–C$_{10}$)alkyl; a is 0, 1, 2, 3 or 4; and Z is —CH$_2$— or —CH$_2$CH$_2$—; where the option substituted phenyl and optionally substituted pyridinyl are each optionally substituted with one to three substituents, each independently selected from the group consisting of hydroxy, fluoro, chloro, iodo, bromo, CF$_3$, sulfonamide, (C$_1$–C$_4$)alkyl, (C$_1$–C$_4$)alkoxy, carboxy, hydroxyalkyl, alkoxycarbonyl, (C$_1$–C$_4$)thioalkyl, sulfonyl, sulfinyl, amino, —NH—CO—(CH$_2$)$_a$-(phenyl), —NH—CO—(C$_1$–C$_{10}$)alkyl, —NH—SO$_2$—(CH$_2$)$_a$-(phenyl) and —NH—SO$_2$—(C$_1$–C$_{10}$)alkyl; and (v) a compound of formula XXI

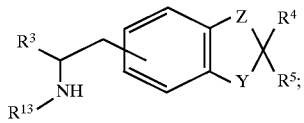

wherein R$^3$ is hydrogen or (C$_1$–C$_6$)alkyl; R$^4$ and R$^5$ are each independently selected from the group consisting of hydrogen, CO$_2$H, CO$_2$R$^6$, CONR$^6$R$^6$, CHO, COR$^6$, CH$_2$OH, CH$_2$OCH$_2$CO$_2$R$^6$ and CH$_2$OCH$_2$CH$_2$OR$^6$ provided that R$^4$ and R$^5$ may not both simultaneously be hydrogen; R$^6$ for each occurence is independently hydrogen or (C$_1$–C$_4$)alkyl; Y is O, S, or NR$^7$; R$^7$ is selected from the group consisting of hydrogen, (C$_1$–C$_{10}$)alkyl, (C$_1$–C$_{10}$)alkenyl, —(CH$_2$)$_a$-(optionally substituted phenyl), —(CH$_2$)$_a$-(optionally substituted pyridinyl), —CO—(CH$_2$)$_a$-(optionally substituted phenyl), —CO—(C$_1$–C$_{10}$)alkyl, —SO$_2$—(CH$_2$)$_a$-(optionally substituted phenyl) and —SO$_2$—(C$_1$–C$_{10}$)alkyl;

R$^{13}$ is —(CH$_2$)$_a$-(optionally substituted phenyl); a is 0, 1, 2, 3 or 4; and Z is —CH$_2$— or —CH$_2$CH$_2$—; where the optionally substituted phenyl and optionally substituted pyridinyl are each optionally substituted with one to three substituents, each independently selected from the group consisting of hydroxy, fluoro, chloro, iodo, bromo, CF$_3$, sulfonamide, (C$_1$–C$_4$)alkyl, (C$_1$–C$_4$)alkoxy, carboxy, hydroxyalkyl, alkoxycarbonyl, (C$_1$–C$_4$)thioalkyl, sulfonyl, sulfinyl, amino, —NH—CO—(CH$_2$)$_a$-(phenyl), —NH—CO—(C$_1$–C$_{10}$)alkyl, —NH—SO$_2$—(CH$_2$)$_a$-(phenyl) and —NH—SO$_2$—(C$_1$–C$_{10}$)alkyl.

This invention also relates to a method of treating a condition selected from the group consisting of diabetes, hyperglycemia and obesity in a mammal, comprising administering to a mammal in need of such treatment an amount of a compound of formula I, or a prodrug thereof, or a pharmaceutically acceptable salt of said compound or prodrug, effective in treating such condition.

This invention also relates to compositions useful for increasing the content of lean meat in animals or poultry, comprising an amount of a compound of formula I, or a prodrug thereof, or a pharmaceutically acceptable salt of said compound or prodrug, effective in increasing said content, and a pharmaceutically acceptable carrier.

This invention also relates to a method of increasing the content of lean meat in animals or poultry comprising administering to an animal or poultry an amount of a compound of formula I, or a prodrug thereof, or a pharmaceutically acceptable salt of said compound or prodrug, effective in increasing said content.

This invention also relates to a method for treating prostate disease such as benign prostatic hypertrophy in a mammal, preferably a human, comprising administering to a mammal in need of such treatment an amount of a compound of formula I, or a prodrug thereof, or a pharmaceutically acceptable salt of said compound or prodrug, effective in treating such disease.

The present invention also relates to a method of treating a condition selected from the group consisting of peptic ulceration, esophagitis, gastritis, duodenitis (including that induced by H. pylori), intestinal ulcerations (including inflammatory bowel disease, ulcerative colitis, Crohn's disease and proctitis), gastrointestinal ulcerations and intestinal motility disorders such as irritable bowel syndrome, in a mammal, preferably a human, comprising administering to a mammal in need of such treatment an amount of a compound of formula I, or a prodrug thereof, or a pharmaceutically acceptable salt of said compound or prodrug, effective in treating such condition.

The present invention also relates to a method for treating depression in a mammal, preferably a human, comprising administering to a mammal in need of such treatment an amount of a compound of formula I, or a prodrug thereof, or a pharmaceutically acceptable salt of said compound or prodrug, effective in treating depression.

The present invention also relates to a method for treating dyslipidemia in a mammal, preferably a human, comprising administering to a mammal in need of such treatment an amount of a compound of formula I, or a prodrug thereof, or a pharmaceutically acceptable salt of said compound or prodrug, effective in treating dyslipidemia.

The present invention also relates to a method of treating airway inflammatory disorders, especially asthma, comprising administering to a mammal in need of such treatment an amount of a compound of formula I, or a prodrug thereof, or a pharmaceutically acceptable salt of said compound or prodrug, effective in treating such disorders.

This invention includes prodrugs of compounds of formula I having free amino, amido, hydroxy or carboxylic groups. Prodrugs are understood to comprise an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, by way of example and not of limitation, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs are also understood to include carbonates, carbamates, amides and alkyl esters which are covalently bonded to the above substituents of formula I through the carbonyl carbon prodrug side chain. Prodrugs also include compounds in which the secondary amine and its β-hydroxy when taken together form a group of the formula

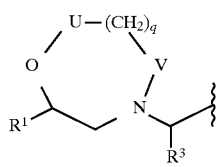

wherein $R^1$ and $R^3$ are as defined in formula I, q is 0 to 6, and U and V are independently carbonyl, methylene, $SO_2$ or $SO_3$, wherein methylene is optionally substituted with hydroxy.

It is noted that certain compounds of formula I, wherein the $R^4$ and $R^5$ moieties terminate in a carboxylic acid ester moiety, are both active compounds and prodrugs. That is, the esters just mentioned are active compounds. They can also hydrolyze in the body to yield the corresponding (free) carboxylic acids which are also themselves active compounds. Such hydrolysis can be desirable since the free acid is selective for the $\beta_3$-subtype adrenergic receptor. $\beta_3$-selectivity reduces or avoids undesirable effects that may be present with $\beta_1$- and/or $\beta_2$-agonism, such as increased heart rate, smooth muscle tremoring, and decreased blood pressure.

It will be appreciated by those skilled in the art that compounds of formula I contain at least one chiral center, and possibly two chiral centers when $R^4$ and $R^5$ are different or when $R^3$ is not hydrogen and three chiral centers when $R^4$ and $R^5$ are different and when $R^3$ is not hydrogen. Accordingly, compounds of formula I may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of the diseases or conditions noted herein, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of the said utilities by the standard tests described hereinafter. In general, (R)-stereochemistry is preferred at all chiral centers in the compounds of this invention.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo", as used herein, unless otherwise indicated, includes chloro, fluoro, bromo and iodo.

The term "treating" as used herein includes preventative as well as disease remitative treatment.

Particular values of $(C_1-C_6)$alkyl include methyl, ethyl, propyl, isopropyl, butyl, isobutyl, t-butyl, pentyl, isopentyl, and hexyl.

Particular values of $(C_1-C_6)$alkoxy include methoxy, ethoxy, propoxy, isopropoxy, butoxy, isobutoxy, t-butoxy, pentoxy, isopentoxy, and hexoxy.

More particular values of $(C_1-C_6)$alkyl include the values of $(C_1-C_3)$alkyl, including methyl, ethyl, propyl, and isopropyl.

More particular values of $(C_1-C_6)$alkoxy include the values of $(C_1-C_3)$alkoxy, including methoxy, ethoxy, propoxy, and isopropoxy.

DETAILED DESCRIPTION

Compounds of formula I can be made by processes which include processes known in the chemical arts. Such processes for the manufacture of a compound of formula I as defined above are provided as further features of the invention and are illustrated by the following procedures in which the meanings of generic radicals are as given above unless otherwise qualified. The processes can be effected, generally:

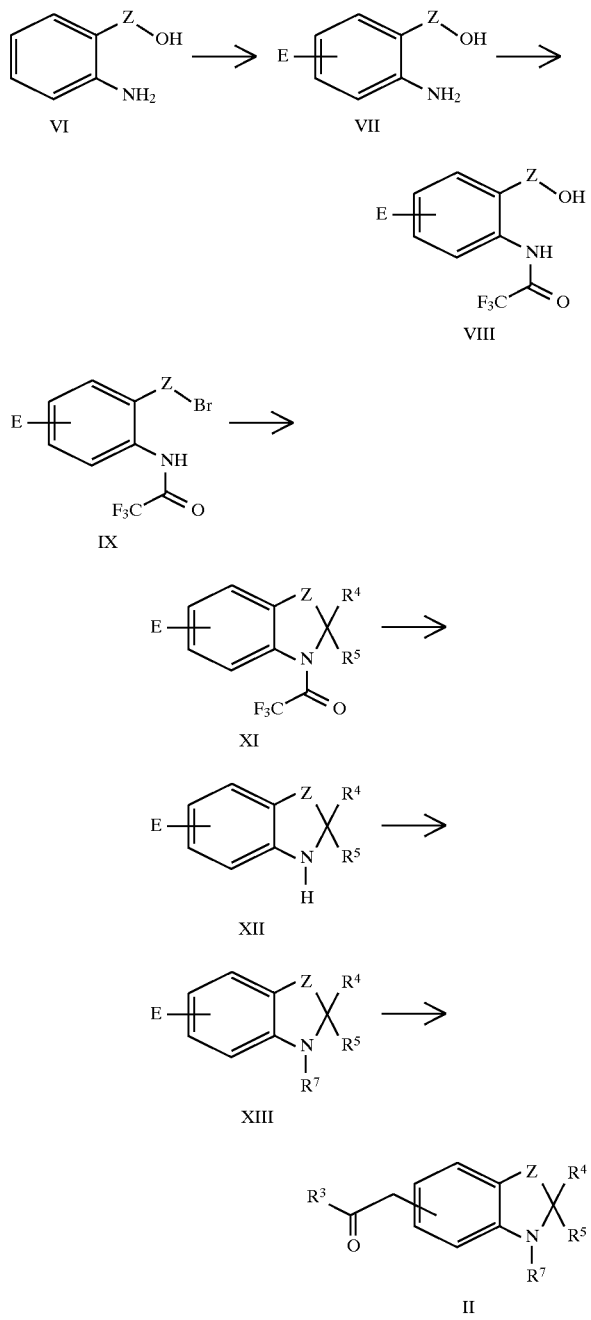

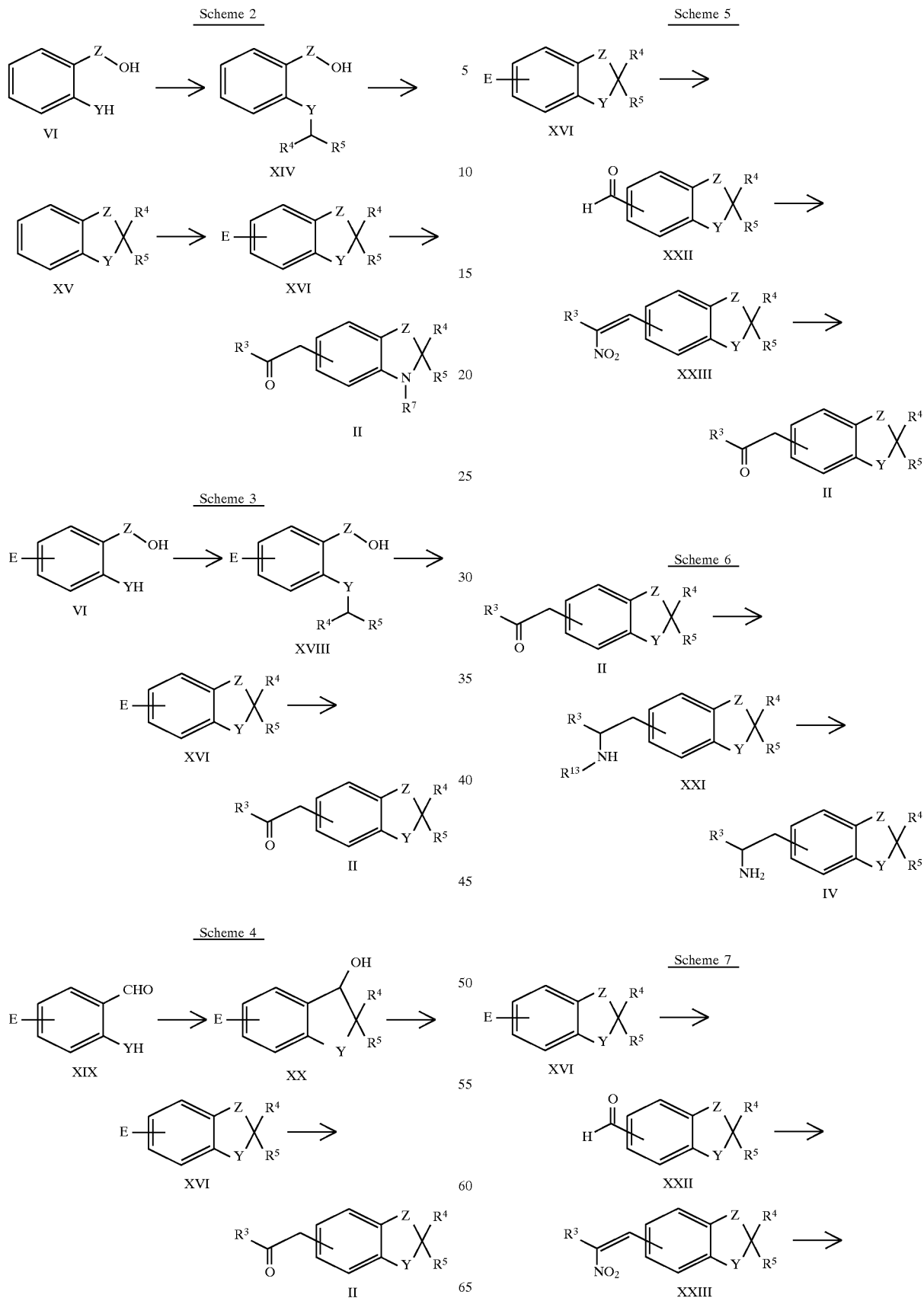

13

-continued
Scheme 7

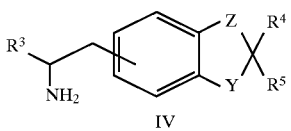

IV

Scheme 8

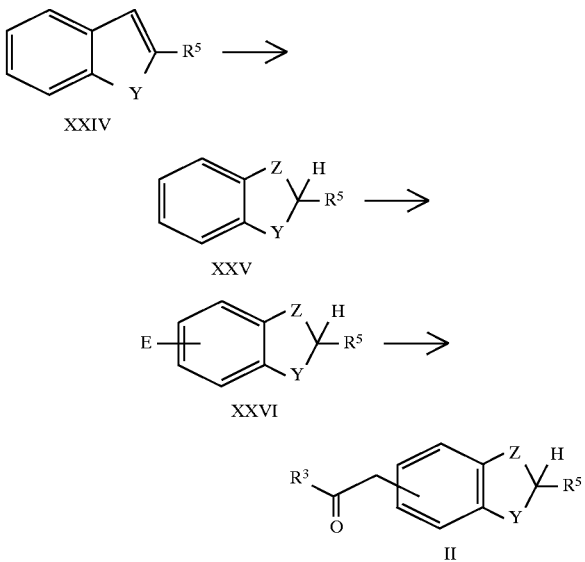

In the discussion which follows, common chemical acronyms and abbreviations have been used: BOC (tert-butoxycarbonyl); Cbz (benzyloxycarbonyl); THF (tetrahydrofuran); DMF (dimethylformamide); DME (dimethoxyethane); DMSO (dimethylsulfoxide); TFA (trifluoroacetic acid). "Lower" as used herein (for example, when referring to a lower alkyl group or a lower alkanol) means ($C_1$–$C_4$).

The expression "reaction inert solvent" refers to any solvent which does not interact with starting materials, reagents, intermediates or products in a manner which adversely affects the reaction or yield of the desired product.

Processes for the manufacture of a compound of formula I as defined above are illustrated by the following procedures in which the meanings of generic radicals are as given above unless otherwise qualified.

(a) A compound of formula I can be synthesized by treating a compound of formula II with a compound of formula III in the presence of an appropriate reducing agent.

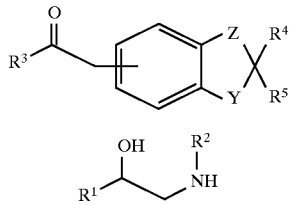

The reaction is conducted by employing a reducing agent such as sodium borohydride, sodium triacetoxyborohydride, or hydrogen in the presence of palladium-on-carbon (e.g., 10%) catalyst. The reaction is typically implemented by stirring in a polar solvent such as a lower alcohol, a lower

14 carboxylic acid, or a chlorinated hydrocarbon, for example methanol, acetic acid, or 1,2-dichloroethane, or a mixture of these solvents.

(b) A compound of formula I, wherein $R^2$ is hydrogen, can also be synthesized by reacting a compound of formula IV with a compound of formula V.

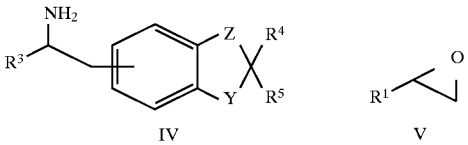

The reaction can be implemented by heating in a solvent, typically a hydrocarbon solvent such as toluene or a more polar solvent such as dimethyl sulfoxide, optionally a mixture of solvents, and optionally in the presence of a catalyst such as (trimethylsilyl)acetamide.

The preparation of intermediate compounds II and IV are described hereinbelow.

If they are not commercially available, the necessary starting materials for the following procedures may be made by procedures which are selected from standard organic chemical techniques, techniques which are analogous to the synthesis of known compounds, or techniques which are analogous to the below described procedures or the procedures described in the examples.

Preparation of a ketone of formula II wherein Y is $NR^7$ is illustrated in Scheme 1. Amino alcohol VI is halogenated to make a halide VII, wherein E is bromo or iodo. The reaction is typically conducted with stirring and at a temperature from about −50° C. to about 70° C. in the presence of a halogenating agent such as iodine or 2,4,6-tetrabromocyclohexa-2,5-dienone. The reaction can be implemented in any reaction inert solvent, such as diethyl ether or dichloromethane.

Halide VII can then be protected by methods analogous to those known in the art to yield amide VIII, for example with an acid anhydride such as trifluoroacetic anhydride, in a reaction inert solvent such as an ether or halogenated hydrocarbon (e.g., diethyl ether or dichloromethane), at room temperature or lower. The reaction is typically conducted with stirring, optionally in the presence of a base such as triethylamine, pyridine or N,N-dimethylaniline.

An amide VII is then converted to a bromide IX by methods analogous to those known in the art, for example with phosphorus tribromide or triphenylphosphine and carbon tetrabromide, in a reaction inert solvent such as an ether or halogenated hydrocarbon (e.g., diethyl ether or dichloromethane), at a temperature from about −10° C. to about 50° C. The reaction is typically conducted with stirring.

A bromide IX can then be treated with an active methine halide of formula $(Br)(H)C(R^4)(R^5)$, for example diethyl bromomalonate, to yield a heterocycle XI. The reaction is typically conducted with stirring in a reaction inert solvent such as THF or DME at a temperature from about −25° C. to about 50° C. in the presence of a base such as sodium hydride or potassium tert-butoxide.

A preferred modification of the above reaction involves premixing the bromide IX with the active methine halide $(Br)(H)C(R^4)(R^5)$ in a reaction inert solvent followed by the addition of the base at the most rapid practical rate. Preferably, the reaction is carried out at about 5° C. A more preferred modification of the above reaction involves premixing a bromide IX with the active methine halide (Br)(H)C($R^4$)($R^5$) in the reaction solvent, and separately premixing the base in the reaction inert solvent, followed by simultaneous addition of both solutions to the reaction vessel at similar rates. Preferably, the reaction is carried out at about 5° C.

A heterocycle XI can then be deprotected by methods analogous to those known in the art to yield the heterocycle XII wherein $R^7$ is H. The reaction is typically conducted with stirring and at room temperature (or higher if preferred), in the presence of a basic catalyst such as sodium methoxide or magnesium methoxide. The reaction can be implemented in a polar solvent such as a lower alcohol, for example methanol.

A heterocycle of formula XII may be treated with a halide $R^7I$, $R^7Br$, or $R^7Cl$ wherein $R^7$ is not H to afford a heterocycle of formula XIII. The reaction is typically conducted with stirring at a temperature from about −80° C. to about 60° C., in the presence of a base such as lithium bis (trimethylsilyl)amide. The reaction can be carried out in an inert ethereal solvent such as THF, optionally in the presence of a dipolar aprotic solvent such as DMF and optionally in the presence of an ionic halide such as sodium iodide.

A heterocycle of formula XIII can then be converted to the ketone of formula II by treatment with an enol ester of formula $CH_2$=CH(OAc)$R^3$, for example isopropenyl acetate. The reaction is typically carried out with stirring at room temperature to about 130° C. in an inert solvent, such as an ethereal or hydrocarbon solvent, for example toluene, in the presence of tri-n-butyltin methoxide, a phosphine such as tri-o-tolyl phosphine, and a palladium catalyst, such as palladium acetate.

Preparation of a ketone of formula II wherein Y is O, S or $NR^7$ is illustrated in Scheme 2. Alcohol VI is treated with an active methine halide of formula (Br)(H)C($R^4$)($R^5$), for example diethyl bromomalonate, to yield a compound of formula XIV. The reaction is typically conducted with stirring, at a temperature of about 0° C. to 100° C., optionally in the presence of a base such as sodium hydride, potassium hydroxide, potassium carbonate, or potassium tert-butoxide. The reaction can be implemented without solvent or in a polar solvent such as a lower alkanol, for example methanol, a lower ketone, for example acetone, acetonitrile, or DMF.

An alcohol of formula XIV can be dehydratively cyclized in a so-called Mitsunobu reaction to make a heterocycle of formula XV. The reaction is typically conducted with stirring and at room temperature (or higher if preferred) in the presence of a dehydrating agent such as a stoichiometric quantity of a diazocarboxyl compound, for example 1,1'-azodi(carbonylpiperidide), and a phosphine, for example triphenylphosphine. The reaction can be implemented in any inert solvent such as THF, DMF, hydrocarbons, or halogenated hydrocarbons.

A heterocycle of formula XV can, if Y is $NR^7$ and $R^7$ is H, be converted to a heterocycle of formula XV, where Y is $NR^7$ and $R^7$ is not H, by treatment with a halide of formula $R^7I$, $R^7Br$, or $R^7Cl$ wherein $R^7$ is not H. The reaction is typically conducted with stirring at a temperature from about −80° C. to about 60° C., in the presence of a base such as lithium bis(trimethylsilyl)amide. The reaction can be carried out in a reaction inert ethereal solvent such as THF, optionally in the presence of a dipolar aprotic solvent such as DMF and optionally in the presence of an ionic halide salt such as sodium iodide.

A heterocycle of formula XV can then be halogenated to afford a halide of formula XVI, wherein E is bromo or iodo. The reaction is typically conducted with stirring and at a temperature from about −50° C. to about 70° C. in the presence of a halogenating agent such as an iodine or 2,4,4,6-tetrabromocyclohexa-2,5-dienone. The reaction can be implemented in any reaction inert solvent, such as diethyl ether or dichloromethane.

A heterocycle of formula XVI can then be converted to a ketone of formula II by treatment with an enol ester of formula $CH_2$=CH(OAc)$R^3$, for example isopropenyl acetate. The reaction is typically carried out with stirring at room temperature to about 130° C. in a reaction inert solvent, such as an ethereal or hydrocarbon solvent, for example toluene, in the presence of tri-n-butyltin methoxide, a phosphine such as tri-o-tolyl phosphine, and a palladium catalyst, such as palladium acetate.

An alternate preparation of a ketone of formula II wherein Y is O, S or $NR^7$ is illustrated in Scheme 3. Halo alcohol XVII, wherein E is bromo or iodo, is treated with an active methine halide of formula (Br)(H)C($R^4$)($R^5$), for example diethyl bromo-malonate, to yield a compound of formula XVIII. The reaction is typically conducted with stirring, at a temperature of about 0° C. to about 100° C., optionally in the presence of a base such as sodium hydride, potassium hydroxide, potassium carbonate, or potassium tert-butoxide. The reaction can be implemented without solvent or in a polar solvent such as a lower alkanol, for example methanol, a lower ketone, for example acetone, acetonitrile, or DMF.

An alcohol of formula XVIII can be cyclized to a heterocycle of formula XVI by conversion of the alcohol to a leaving group, such as chloro, bromo, iodo, p-tosyl, or mesyl, followed in a second step by treatment with a base to effect the cyclization. For example, the alcohol can be converted to a mesyl group by treatment with methanesulfonyl chloride in the presence of triethylamine. This reaction is typically conducted with stirring in a reaction inert solvent such as an ether or halogenated hydrocarbon, at a temperature of about −50° C. to about 75° C. The subsequent treatment with base is typically carried out with stirring in a polar aprotic solvent such as acetonitrile, THF, or a lower ketone, for example, methyl ethyl ketone, at room temperature to about 120° C. Suitable bases include potassium carbonate, potassium tert-butoxide, or sodium hydride.

A heterocycle of formula XVI can then be converted to a ketone of formula II by treatment with an enol ester of formula $CH_2$=CH(OAc)$R^3$, for example isopropenyl acetate. The reaction is typically carried out with stirring at room temperature to about 130° C. in a reaction inert solvent, such as an ethereal or hydrocarbon solvent, for example toluene, in the presence of tri-n-butyltin methoxide, a phosphine such as tri-o-tolyl phosphine, and a palladium catalyst, such as palladium acetate.

An alternate preparation of a ketone of formula II wherein Y is O, S or $NR^7$ and Z is —$CH_2$— is illustrated in Scheme 4. Halo aldehyde XIX, wherein E is bromo or iodo, is treated with an active methine halide of formula (Br)(H)C($R^4$)($R^5$), for example diethyl bromomalonate, to yield a compound of formula XX. The reaction is typically conducted with stirring, at a temperature of about 0° C. to about 120° C., in the presence of a base such as sodium hydride, potassium carbonate, or potassium tert-butoxide. The reaction can be implemented in a polar aprotic solvent such as acetonitrile, DME, or a lower ketone, for example methyl ethyl ketone.

An alcohol XX can be reduced to a heterocycle XVI by methods known to one skilled in the art, for example with triethylsilane. This transformation is typically carried out with stirring at a temperature from about −20° C. to 120° C., optionally in a reaction inert solvent such as an ether, halogenated hydrocarbon, or hydrocarbon solvent, for example toluene, and optionally in the presence of an acid catalyst, for example trifluoroacetic acid.

A heterocycle of formula XVI can then be converted to a ketone of formula II by treatment with an enol ester of formula $CH_2=CH(OAc)R^3$, for example isopropenyl acetate. The reaction is typically carried out with stirring at room temperature to about 130° C. in a reaction inert solvent, such as an ethereal or hydrocarbon solvent, for example toluene, in the presence of tri-n-butyltin methoxide, a phosphine such as tri-o-tolyl phosphine, and a palladium catalyst, such as palladium acetate.

An alternate preparation of a ketone of formula II wherein Y is O, S or $NR^7$ and Z is $—CH_2—$ is illustrated in Scheme 5. A compound of formula XVI can be treated with carbon monoxide and a reducing agent, such as hydrogen or sodium formate, in the presence of a catalyst, such as palladium tetrakis(triphenylphosphine), to afford an aldehyde of formula XXII. The reaction is typically carried out with stirring in a suitable reaction inert solvent, such as an ether, hydrocarbon, halogenated hydrocarbon, or pyridine, in the presence of a base such as triethylamine, potassium carbonate, or pyridine.

An aldehyde of formula XXII can be converted to a nitro compound of formula XXIII by treatment with a nitro compound of formula $R^3CH_2NO_2$. This reaction can be carried out by methods known to one skilled in the art, and is typically carried out with stirring in the presence of a base such as potassium tert-butoxide or n-butylamine, at a temperature between room temperature to about 150° C. Suitable solvents for this reaction include hydrocarbons, ethers, and lower alcohols.

A nitro compound of formula XXIII can be converted to the ketone of formula II by hydrolysis with an acid, for example hydrochloric acid, in the presence of a reducing agent such as a powdered metal, for example iron powder. The reaction is typically effected with stirring, optionally in a solvent such as a lower alcohol, water, or an ether such as DME or 1,4-dioxane, at a temperature between about 0° C. and about 130° C.

The preparation of an amine of formula IV wherein Y is O, S or $NR^7$ is illustrated in Scheme 6. A compound of formula II can be converted to an amine of formula XXI by reductive amination with an amine of formula $R^{13}NH_2$, wherein $R^{13}$ is an amine protecting group such as benzyl or (substituted) benzyl. This reaction can be carried out by methods analogous to those known to one skilled in the art, typically in the presence of a reducing agent such as sodium cyanoborohydride, sodium triacetoxyborohydride, sodium borohydride, or hydrogen and a catalyst, for example platinum oxide or Raney nickel. Suitable reaction solvents for this reaction include acetic acid, chlorinated hydrocarbons, THF, and lower alcohols, for example ethanol. It is generally conducted at temperatures from about −50° C. to about 70° C.

An amine of formula XXI can be converted to an amine of formula IV by removal of the group $R^{13}$. This reaction can be carried out by methods analogous to those known to one skilled in the art, and is typically carried out with hydrogen in the presence of a catalyst, such as palladium on carbon. Alternatively, acidic reagents, for example trifluoroacetic acid, may be used to remove the group $R^3$. The reaction is typically carried out with stirring at a temperature of about −30° C. to about 120° C., in a suitable solvent such as an ether or lower alcohol, for example ethanol.

An alternate preparation of an amine of formula IV wherein Y is O, S or $NR^7$ is illustrated in Scheme 7. A compound of formula XVI can be treated with carbon monoxide and a reducing agent, such as hydrogen or sodium formate, in the presence of a catalyst, such as palladium tetrakis(triphenylphosphine), to afford an aldehyde of formula XXII. The reaction is typically carried out with stirring in a suitable reaction inert solvent, such as an ether, hydrocarbon, halogenated hydrocarbon, or pyridine, in the presence of a base such as triethylamine, potassium carbonate, or pyridine.

An aldehyde of formula XXII can be converted to a nitro compound of formula XXIII by treatment with a nitro compound of formula $R^3CH_2NO_2$. This reaction can be carried out by methods known to one skilled in the art, and is typically carried out with stirring in the presence of a base such as potassium tert-butoxide or n-butylamine, at a temperature between room temperature to about 150° C. Suitable solvents for this reaction include hydrocarbons, ethers, and lower alcohols.

A nitro compound of formula XXIII can be reduced to afford an amine of formula IV by treatment with hydrogen in the presence of a catalyst, such as palladium on carbon. The reaction is typically carried out with stirring at about 0° C. to about 70° C., in a suitable solvent such as a lower alcohol, for example methanol, optionally in the presence of an acid, for example hydrochloric acid.

Scheme 8 illustrates the synthesis of compounds of formula II wherein $R^4$ is H and Z is $—CH_2—$. A heterocycle of formula XXIV can be reduced to afford the corresponding dihydro compound of formula XXV. This reaction can be carried out by methods analogous to those known to one skilled in the art, for example by the use of sodium borohydride, magnesium metal, or hydrogen in the presence of a catalyst, for example palladium on carbon or Raney nickel. The reaction is typically carried out with stirring, at a temperature between about 0° C. and about 120° C., in a suitable solvent such as acetic acid or a lower alcohol, for example methanol.

A heterocycle of formula XXV can then be halogenated to afford a halide of formula XXVI, wherein E is bromo or iodo. The reaction is typically conducted with stirring and at a temperature from about −50° C. to about 70° C. in the presence of a halogenating agent such as a iodine or 2,4,4, 6-tetrabromocyclohexa-2,5-dienone. The reaction can be implemented in any reaction inert solvent, such as diethyl ether or dichloromethane.

A heterocycle of formula XXVI can then be converted to a ketone of formula II wherein $R^4$ is H and Z is $—CH_2—$ by treatment with an enol ester of formula $CH_2=CH(OAc)R^3$, for example isopropenyl acetate. The reaction is typically carried out with stirring at room temperature to about 130° C. in a reaction inert solvent, such as an ethereal or hydrocarbon solvent, for example toluene, in the presence of tri-n-butyltin methoxide, a phosphine such as tri-o-tolyl phosphine, and a palladium catalyst, such as palladium acetate.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

Certain of the compounds of formula I, for example those which have free carboxylic acid functionality, form pharmaceutically-acceptable cation salts by reacting the free acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The amino acid prodrugs of this invention are readily prepared by conventional peptide coupling reactions coupling a free amino or carboxylic group of the compound of formula I with an amino acid or a polypeptide, e.g. dipeptide, chain. The coupling reaction is generally conducted at a temperature of about −30° to about 80° C., preferably about 0° to about 25° C. Suitable coupling reagents are usually present, such as dicyclohexylcarbodiimide with hydroxybenzotriazole (HBT), N-3-dimethylaminopropyl-N'-ethylcarbodiimide with HBT, 2-ethoxy-1-ethoxycarbonyl-1,2-dihydroquinoline, carbonyl diimidazole with HBT, or diethylphosphoryl-cyanide. The reaction is generally conducted in an inert solvent such as acetonitrile, methylene chloride, chloroform, dimethylformamide, dioxane, tetrahydrofuran, dimethoxyethane, or water, or a mixture of two or more such solvents.

Ester, carbonate or carbamate prodrugs of this invention are readily prepared by reaction of a free hydroxyl or amino group of the compound of formula I with an activated carbonyl containing molecule such as acetyl chloride or ethyl chloroformate. The reaction can be carried out neat or in the presence of a reaction inert solvent such as methylene chloride, at a temperature from about −78° to about 100° C. Alcohols can also be reacted with cyanogen chloride in the presence of a Lewis acid to form carbamates.

Prodrugs in which the secondary amine and its β-hydroxy, taken together, form a group of the formula

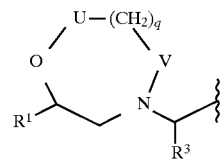

are formed by methods analogous to those described in U.S. Pat. No. 4,593,023, European Patent Application 170,135A published on Jul. 21, 1984 and U.S. Pat. No. 4,607,033.

When treating any of the conditions, disorders and/or diseases previously disclosed herein, generally satisfactory results are obtained when the compounds of the formula (I), prodrugs, or pharmaceutically acceptable salts thereof (hereinafter also referred to herein as "active ingredients or compounds") are administered to mammals, including man or poultry, via either the oral or the parenteral route. Administration by the oral route is prefer red, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 20 mg/kg body weight of the subject per day, preferably about 0.1 to about 10 mg/kg body weight per day, administered singly or as a divided dose. However, the optimum dosage for the individual subject being treated will be determined by the person responsible for the treatment, generally smaller doses being administered initially and thereafter increasing increments made to determine the most suitable dosage. This will vary according to the particular compound employed and with the subject being treated.

The compounds of the present invention are used in combination with a pharmaceutically acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally, for example, intramuscularly, intravenously or subcutaneously. For parenteral administration the compounds can be combined with sterile aqueous or organic media to form injectable solutions or suspensions. Solutions or suspensions of these active compounds can be prepared in water suitably mixed with a surfactant such as hydroxypropylcellulose. Dispersions can also be prepared in sesame or peanut oil, ethanol, water, polyol (e.g., glycerol, propylene glycol and liquid polyethylene glycol), suitable mixtures thereof, vegetable oils, N-methyl glucamine, polyvinylpyrrolidone and mixtures thereof in oils as well as aqueous solutions of water-soluble pharmaceutically acceptable salts of the compounds. Under ordinary conditions of storage and use, these preparations contain a preservative to prevent the growth of microorganisms. The injectable solutions prepared in this manner can then be administered intravenously, intraperitoneally, subcutaneously, or intramuscularly, with intramuscular administration being the preferred parenteral route in man.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The effective dosage of the active ingredient employed may vary depending on the particular compound employed, the mode of administration, the condition being treated and the severity of the condition being treated.

As a consequence of their action in reducing body fat (lipolysis) the compounds of the present invention possess utility for increasing lean meat deposition and/or improving the lean meat to fat ratio in animals, especially ungulate animals such as swine, cattle, sheep, and goats, and poultry. Compounds of formula I can additionally be used for the treatment of obese household pets, for example companion animals such as dogs and cats. The administration of a compound of formula I can be effected orally or parenterally. An amount of a compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantageous veterinary features. For the pet owner or veterinarian who wishes to increase leanness and trim unwanted fat from pet animals, the present invention provides the means by which this can be accomplished. For poultry and swine raisers, using the method of the present invention yields leaner animals which command higher prices from the meat industry.

The compounds of this invention may be tested for hypoglycemic activity according to the following procedure and as an aid in determining dosages when compared to other compounds and standards.

Five to eight week old C57 BL/6J-ob/ob mice (obtained from Jackson Laboratory, Bar Harbor, Me.) are housed five per cage under standard animal care practices. After a one week acclimation period, the animals are weighed and 25 microliters of blood is collected via an ocular bleed prior to any treatment. The blood sample is immediately diluted 1:5 with saline containing 2% sodium heparin, and held on ice for glucose analysis. Animals are then regrouped, in groups of five per cage, such that the mean glucose values of the groups are similar, dosed daily for five days with test compound (0.01–20 mg/kg), a positive control such as englitazone or ciglitazone (50mg/kg p.o.), (U.S. Pat. No. 4,467,902; Sohda et al., *Chem. Pharm. Bull.*, vol. 32, pp. 4460–4465, 1984)), or vehicle. All compounds are administered by oral gavage in a vehicle consisting of 0.25% w/v methyl cellulose. On day 5, the animals are weighed again and bled (via the ocular route) for blood glucose levels. The freshly collected samples are centrifuged for two minutes at 10,000×g at room temperature. The supernatant is analyzed for glucose, for example, with the ABA 200 Bichromatic Analyze™ (a registered trademark of Abbott Laboratories, Diagnostics Division, 820 Mission Street, So. Pasadena, Calif. 91030), using the A-gent™ glucose UV reagent system (hexokinase method) (a modification of the method of Richterrich and Dauwalder, Schweizerische Medizinische Wochenschrift, 101, 860 (1971)), using 20, 60 and 100 mg/dl standards. Plasma glucose is then calculated by the equation:

Plasma glucose (mg/dl)=Sample value×5×1.67=8.35×Sample value
where 5 is the dilution factor and 1.67 is the plasma hematocrit adjustment (assuming the hematocrit is 40%).

The animals dosed with vehicle maintain substantially unchanged hyperglycemic glucose levels (e.g., 250 mg/dl), while positive control animals have depressed glucose levels (e.g., 130 mg/dl). The glucose lowering activity of test compounds is expressed in terms of % glucose normalization. For example, a glucose level which is the same as the positive control is expressed as 100%.

Selectivity of a compound for $\beta_3$-receptors over $\beta_2$ and $\beta_1$ receptors may be determined using the following procedures.

In vitro selectivity may be determined by measurement of cyclic adenosine mono-phosphate (cAMP) accumulation in Chinese hamster ovary cells. Chinese hamster ovary cells uniquely transfected with the gene for the human $\beta_1$, $\beta_2$ or $\beta_3$ receptor are grown to confluence in Ham's F12 media (Gibco BRL, Life Technologies, Inc., Grand Island, N.Y.) containing 10% fetal bovine serum, 500 mg/ml Geneticin, 100 U/ml penicillin, 100 mg/ml streptomycin and 250 ng/ml fungizone according to the procedure described in American Type Culture Collection Catalogue of Cell Lines and Hybridomas, Seventh Edition, 1992, p.36, ATCC CCL 61 CHO-K1. Compounds are prepared as 10 mM stock solutions in DMSO (0.1% DMSO, final concentration), diluted in Ham's F12 media and added to the cells at $10^{-10}$–$10^{-5}$M along with $10^{-3}$M isobutylmethylxanthine to inhibit phosphodiesterase activity. The media and cells are then incubated for 5 minutes at 37° C. At the end of this period, the media is aspirated and the cells lysed in 0.01N HCl. The cellular content of cAMP can then be determined by radioimmunoassay (RIA) using a kit from New England Nuclear (Burlington, Mass.). There is a direct correlation between the cellular content of cAMP and the agonism of the $\beta_1$, $\beta_2$, or $\beta_3$ receptor. The non-selective adrenergic agonist, norepinephrine, is included as a positive control at $10^{-5}$M. Data are expressed as fold increase over basal.

In vivo efficacy may be determined by measurement of oxygen consumption and ambulatory activity on male Sprague-Dawley rats (Charles River, Wilmington, Mass.). Whole animal oxygen consumption may be measured using an open circuit, indirect calorimeter (Oxymax™, from Columbus Instruments, Columbus, Ohio). The Oxymax gas sensors are calibrated with nitrogen ($N_2$) gas and gas mixture (0.5% carbon dioxide ($CO_2$), 20.5% oxygen ($O_2$), 79% $N_2$; (Abco Industrial Supplies, Waterford, Conn.) before each experiment. Rats (male, Sprague Dawley, 300–380 g body weight) are placed in sealed chambers (43×43×10 cm) of the calorimeter and the chambers placed in activity monitors. Air flow rate through the chambers is set at 1.6–1.7 l/min. The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis; ambulatory activity is recorded when two consecutive beams are broken (repeated interruptions of the same beam are not registered) and the results are recorded as counts. Basal oxygen consumption and ambulatory activity can be measured every 10 minutes for 2.5 to 3 hours. At the end of the basal period, the chambers are opened and the test compound (0.01 to 20 mg/kg, prepared in water or other suitable vehicle) or an equivalent volume of vehicle is administered by oral gavage. Oxygen consumption and ambulatory activity can be measured every 10 minutes for an additional three hours post-dosing. Percent change in oxygen consumption may be calculated by averaging the post-dosing values for 2.5 hours and dividing by basal oxygen consumption (average of the predosing values except the first hour). Oxygen consumption values obtained during time periods where ambulatory activity exceeds 100 counts are excluded from the calculation. Thus, the values represent % change in resting oxygen consumption.

In vivo selectivity for $\beta_1$ and $\beta_2$ adrenergic receptors may be determined by measurements of heart rate, blood pressure and plasma potassium concentration gathered on conscious catheterized rats (male, Sprague Dawley, 300–380 g body weight). To implant catheters, rats are anesthetized with pentobarbital (50–60 mg/kg, i.p.) and the left carotid artery is cannulated with PE50 tubing. The catheter is tunneled subcutaneously, exteriorized at the back of the neck, filled with a solution of polyvinylpyrrolidone in heparinized saline, flame-sealed and taped. Experiments are performed 7 days after surgery. On the day of the experiment, the catheters are untaped and flushed with saline. After at least 30 minutes, basal values for heart rate and blood pressure are measured by attaching the catheter to a pressure transducer, the results recorded on a Grass Model 7 polygraph (Grass Medical Instruments, Quincy, Mass.), and a basal blood sample (0.5 ml) is obtained from the arterial catheter. After obtaining basal values, the test compound or vehicle is administered by oral gavage, and blood pressure (measure of $\beta_2$ activity) and heart rate (measure of $\beta_1$ activity) measurements are taken at 15, 30, 45 and 60 minutes and blood samples for potassium determination ($\beta_2$) are obtained at 30 and 60 min. Isoproternol, a non-selective $\beta$-agonist can be tested as a positive control at doses ranging from 0.001 to 1 mg/kg (injected s.c. in saline vehicle). Plasma potassium is determined by flame spectrophotometry. To determine changes, basal values are subtracted from the average of the post dosing values.

Compounds of the formula I also have the effect of reducing intestinal motility and thus find utility as aiding in the treatment of various gastrointestinal disorders such as irritable bowel syndrome, peptic ulceration, esophagitis, gastritis and duodenitis, (including that induced by *H. pylori*), intestinal ulcerations (including inflammatory bowel disease, ulcerative colitis, Crohn's disease and proctitis) and gastrointestinal ulcerations. It has been proposed that the motility of non-sphincteric smooth muscle contraction is mediated by activity at $\beta_3$ adrenergic receptors. The availability of a $\beta_3$ specific agonist, with little activity at $\beta_1$ and $\beta_2$ receptors will assist in the pharmacologic control of intestinal motility without concurrent cardiovascular effects.

In vivo activity of the compounds of formula I for the treatment or prevention of intestinal motility disorders can be determined according to the following procedures. Eighteen-hour fasted male Sprague Dawley derived (CD) rats (175–225 grams) are dosed with 0.01–20 mg/kg p.o. of compound or vehicle (distilled water). Thirty minutes after administration of compound, the rats are orally dosed with 0.25 ml of a solution of sodium chromate in 0.9% saline containing about 20,000 cpm of $^{51}$Cr (specific activity 350 mCi/mg Cr). Twenty minutes later, the rats are sacrificed, the gastroesophageal, pyloric, and ileocecal junctions are then ligated, and the stomachs and small intestines removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}$Cr in each segment times the segment number: geometric center=S ((fraction of $^{51}$Cr per segment)×(segment number)). For these calculations the stomach may be considered segment number 0, and the ten intestinal segments as numbers 1 to 10. Thus, a geometric center of 0.0 would indicate that the entire load of $^{51}$Cr had remained in the stomach. Data from two experiments may be pooled, and statistical evaluations can be made using Dunnett's multiple comparison test.

Alternatively, in groups of 8, overnight-fasted male Sprague-Dawley (CD) rats (175–225 grams) may be anesthetized with methoxyflurane. A small abdominal incision is then made, and the pylorus ligated. Immediately after the ligation, a solution of compound or the vehicle (distilled water) is injected into the proximal duodenum. The doses of compound used should be 0.01–20 mg/kg. The incisions can then be closed and the rats can be allowed to recover from the anesthesia. Two hours after the ligation the rats are sacrificed and the gastric fluid collected and cleared by centrifugation. Total volume of secretion can be determined by weight, and acidity can be determined by titration to pH 7.0 with 0.1N NaOH using an automatic titrator (Radiometer TTT85). The data from two experiments are then pooled. A group of rats treated with 10 mg/kg of the antisecretory histamine $H_2$-receptor antagonist cimetidine may be included in each experiment as a positive control. Statistical evaluations can be made using Student's t-test.

In vitro activity for relaxation of contracted ileum from isolated guinea pig ileum can be determined according to the following procedure. Fresh isolated segments of guinea pig ileum (about 1.5 cm long) are mounted in tissue baths containing Tyrode's physiological salt solution at about 30° C. and aerated continuously with $O_2:CO_2$ (95%:5%). Tissues are then equilibrated for 60–90 minutes under 4.0 gm tension in order to achieve stable baselines. Histamine is then added to the baths in a cumulative fashion in concentrations ranging from 1 nM to 10 mM. The maximum tension generated after each addition of histamine is recorded on a Grass Physiograph (Grass Medical Instruments, Quincy, Mass.). The tissues are then washed with several changes of Tyrode's solution, basal tension can be readjusted to 4.0 grams, and a stable baseline is then again obtained. Each tissue may then be exposed to a single concentration of a compound (range 1 nM to 10 mM) or vehicle and after a 30 minute equilibration period, the histamine does response curve may then be repeated. Results from multiple experiments are standardized (0–100%) to the maximum response of the control tissues and plotted as percent maximum tension versus the log of the histamine concentration in the absence and presence of the compound.

In vivo activity of compounds of formula I to protect against gastric ulcerations can be determined according to the following procedure.

Food (but not water) was withheld for 24 h from female Sprague Dawley rats (Charles River, Wilmington, Mass.) weighing 70–120 g. Access was then allowed to food for 90 min. A single dose of b-adrenoceptor agonist was then administered p.o. (1 ml 100 g$^{-1}$). Indomethacin (purchased from Sigma Chemical Co., St. Louis, Mo.) (60 mg kg$^{-1}$, 1 ml 100 g$^{-1}$ body weight) was then injected subcutaneously. Control rats received the subcutaneous injection of indomethacin and oral administration of vehicle (0.5% methyl cellulose in distilled water) for the b-adrenoceptor agonist. The animals were then allowed continued access to food but water was withdrawn. The animals were sacrificed by cervical dislocation 6 hours after dosing with indomethacin. The stomachs were removed, opened along the greater curvature and washed in 0.9% saline. An assessment of gastric damage was carried out by an observer who was unaware of the dosing regimen. A transparent plastic grid divided into 1 mm$^2$ sections was placed over the antrum and the area of macroscopic damage assessed as the total area of visible lesions in mm$^2$. This value was then expressed as a percentage of the total antral area.

Compounds of formula I can be assessed for antidepressant activity in vivo according to the following procedure.

Male CD1 mice weighing between 20 and 25 g, and Sprague-Dawley rats weighing between 200 and 250 g, may be obtained from Charles River (Wilmington, Mass.). Compounds of formula I are dissolved in water. The compounds may be administered to mice in a volume of 10 ml kg$^{-1}$, and to rats in a volume 2 ml kg$^{-1}$. Control animals receive the vehicle. Positive test results for the following parameters indicate antidepressant activity.

I. Antagonism of hypothermia induced by reserpine:

Mice are given reserpine (2.5 mg kg$^{-1}$ i.p. dissolved in 1% citric acid). Their rectal temperatures may be measured 3.5 h later. The mice may then be divided into different groups so as to obtain the same mean rectal temperature in each group. Half an hour later (i.e., 4 h after reserpine), the mice are given the vehicle or compound. Rectal temperature can be measured again 90 min later (i.e., 5 hours and 30 min after the injection of reserpine) (Bourin et al., The Value of the Resernine Test in Psychopharmacology. Arzneim. Forsch. 33, 1173, (1983)).

II. Antagonism of hypothermia induced by apomorphine:

Half an hour after the mice are placed in individual cages, their rectal temperatures are recorded. The animals should be allocated so as to obtain the same mean rectal temperature in each group. Apomorphine (16 mg kg$^{-1}$, s.c.) can be given 30 min after the compound or its vehicle. Rectal temperature can be measured again 30 min after the apomorphine treatment (Puech et al, Antagonism of Hypothermia And Behavioral Response To Apomorphine; A Simple, Rapid And Discriminating Test For Screening Antidepressants And Neuroleptics, Psychopharmacology 75, 84, (1981)).

III. Effect on learned helplessness behavior:

This test is performed basically as described by Giral et al. Reversal Of Helpless Behavior In Rats By Putative 5-HT$_{1A}$ Agonists. Biol. Psychiat. 23, 237. (1988). Electric foot-shocks are delivered to male albino Sprague-Dawley rats placed in chambers (20×10×10 cm) with Plexiglass® walls and covers. The floors are made of stainless-steel grids (1.5 cm mesh). A constant-current shock is delivered as 60 scrambled, randomized inescapable shocks (15 s duration, 0.8 mA, every 60+15 s) to the grid floor. Control rats are then placed in identical chambers for 1 h but no shock is administered. All preconditioning trials are performed on day 1 between 9 and 11 a.m. Avoidance training is initiated 48 h (day 3) after inescapable shock in automated two-way shuttle-boxes (60×21×30 cm) with Plexiglass® walls and a floor consisting of stainless-steel rods spaced 1.0 cm apart in order to evaluate escape deficits. Each shuttle-box is divided into two chambers of equal size by a stainless-steel partition, with a gate providing access to the adjacent compartment through a 7×7 cm space. Shuttle-box sessions are performed for 3 consecutive days (days 3, 4 and 5). The animals are placed individually in the shuttle-box and allowed to habituate to the environment for 5 min (for the first session only) and then subjected to 30 trials. The intertrial interval should be 30 seconds. A light signal, used as a conditioned stimulus, is presented during the first 3 seconds of each trial. Crossing the gate into the other compartment of the box during this 'conditioned-stimulus only' period (referred to as avoidance response) allows the rats to avoid shocks. A period with conditioned stimulus plus electric foot-shock (0.8 mA) may be presented if an avoidance response does not occur. Crossing the gate into the other compartment during this conditioned stimulus plus shock period is referred to as an escape response. Absence of escape response during the 3-second duration conditioned stimulus plus shock should be considered to be an escape failure.

The rats (n=10 per group) should be treated randomly according to one of the following protocols: the control sample, which receives no shock, and is given vehicle; experimental animals with inescapable shock are treated daily with vehicle or compound. Animals should be treated orally over 5 consecutive days, i.e. 6 hours after shock pretreatment on day 1, and then twice per day, a half dose in the morning (30 min before shuttle-box session) and a half dose in the afternoon (except on the 5th day). Statistical analysis can be performed on the mean number of escape failures using a two-way analysis of variance (subjects X sessions) followed by Dunneft's test.

Compounds of formula I also have the effect of bronchial relaxation and increased ciliary motility and thus may be useful in the treatment of airway inflammatory disorders such as asthma and obstructive lung disease. In vitro activity of compounds for the treatment of airway inflammatory disorders can be determined by measurement of guinea-pig bronchial ring relaxation according to the following procedure.

Guinea-pig main bronchial rings are obtained from tri-colored guinea-pigs of either sex (250–350 g) anesthetized with urethane (1.25 g kg$^{-1}$, i.p.) and are suspended under an initial tension of 2.0 g in Krebs solution at 37° C. gassed with 95% $O_2$:5% $CO_2$. After about 1 hour of equilibration, guinea-pig bronchial rings are contracted with acetylcholine ($10^{-3}$M) and relaxed to maximal relaxation with theophylline ($3\times10^{-3}$M), then allowed to equilibrate for a further 60 min while they are washed with Krebs solution every 15 min.

Changes in tension are measured isometrically with strain gauges and amplifiers and displayed on a recorder. The composition of the Krebs solution is (mM): NaCl 118.0, KCl 5.4, CaCl$_2$ 2.5, KH$_2$PO$_4$ 1.2, MgSO$_4$ 1.2, NaHCO$_3$ 25.0 and glucose 11.7.

To test effects of compounds on resting tension, cumulative concentration-response curves are obtained by addition of the test compounds ($10^{-9}$ to $10^{-6}$M) every 10–20 min until a plateau is reached. The relaxant effects of the compounds are expressed as percentages of the maximal relaxation induced by theophylline ($3\times10^{-3}$M).

In vitro activity of the compounds of formula I for prostate disease can be determined according to the following procedures.

Ventral prostates of male Sprague-Dawley rats (300–400 g) anesthetized with diethyl ether are quickly excised and placed in oxygenated Krebs solution. While maintained at room temperature in this buffer, adherent fatty and connective tissues are removed. The prostates are then suspended in 10-ml organ baths containing Krebs solution warmed to 37° C. and aerated with a mixture of 95% $O_2$ and 5% $CO_2$. The composition of the Krebs solution is 118.4 mM NaCl, 4.7 mM KCl, 1.2 mM MgSO$_4$, 2.5 mM CaCl$_2$, 11.1 mM dextrose, 25.0 mM NaHCO$_3$ and 1.2 mM KH$_2$PO$_4$, dissolved in distilled and demineralized water. The tissues are attached to isometric force-displacement transducers and isometric contraction is recorded under a loading tension of 0.5 g. Equilibration is undertaken for 1 or 2 hr before the addition of test compounds. Submaximal contractions are first elicited by repeated concentrations of $1\times10^{-6}$M phenylephrine until constant responses are obtained. The control and test compound-treated experiments are done in different preparations. A concentration-response curve to cumulate concentrations of phenylephrine or acetylcholine ($10^{-9}$ to $10^{-4}$M) is determined. For testing compounds, a concentration response curve to phenylephrine or acetylcholine is determined in the presence of the compounds.

In vitro activity of compounds of formula I can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 ml Krebs-Henseleit solution of the following composition (mM): NaCl 112, KCl 5.9, MgCl$_2$ 1.2, CaCl$_2$ 2, NaHCO$_3$ 25, NaHPO$_4$ 1.2, glucose 11.5. The medium is maintained at 37° C. and at pH 7.4, and is equilibrated with a gas mixture consisting of 95% $O_2$ and 5% $CO_2$. A resting tension of 0.5 g is applied and the responses are recorded isometrically through a force-displacement transducer. The preparations are equilibrated for 90 min before starting the experiments.

Concentration-response curves for phenylephrine or acetylcholine ($10^{-9}$ to $10^{-4}$M) are determined by adding the compound directly to the bathing media in a cumulative fashion. For testing compounds, the prostate strips are incubated in the presence of compound (1 or 10 μM) for 30 minutes before and then phenylephrine or acetylcholine are added to the medium in a cumulative fashion to obtain to the concentration-response curve in the presence of the compound.

Compounds of the formula I lower triglyceride levels and cholesterol levels and raise high density lipoprotein levels and are therefore of use in combating medical conditions wherein such lowering (and raising) is thought to be beneficial. Thus, the compounds of formula I can be used in the treatment of hypertriglyceridaemia, hypercholesterolemia and conditions of low HDL (high density lipoprotein) levels in addition to the treatment of atherosclerotic disease such as of coronary, cerebrovascular and peripheral arteries, cardiovascular disease and related conditions.

The compounds may also be combined with other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors, for example lovastatin, simvastatin and pravastatin; inhibitors of cholesterol absorption, for example beta-sitosterol and acyl CoA; cholesterol acyltransferase inhibitors, for example melinamide; anion exchange resins for example cholestyramine, colestipol or dialkylaminoalkyl derivatives of a cross-linked dextran; nicotinyl alcohol, nicotinic acid or a salt thereof; vitamin E; and thyromimetics.

Activity of compounds of formula I for dyslipidemia can be determined according to the following procedure. C57BL/6J ob/ob mice (male, 30–40 g body weight, Jackson Lab, Bar Harbor, Me.), housed 5 mice per cage in an environmentally controlled room, can be dosed once daily for 3 weeks with compound (0.01–20 mg/kg, n=15 per group) or vehicle (saline) by oral gavage. Body weight of each mouse can be measured daily and food intake per cage is determined by weighing the amount of food left in the trough. At the end of the study, 24 h after giving the final dose of compound, the mice may be sacrificed by decapitation and blood collected. Plasma concentrations of glucose, free fatty acids and triglyceride can be determined with the VP Super System Autoanalyzer (Abbott, Irving, Tex.).

Activity of compounds of formula I for decrease in body fat can be determined according to the following procedure. C57BL/6J ob/ob mice (male, 30–40 g body weight, Jackson Lab, Bar Harbor, Me.) are housed 5 mice per cage in an environmentally controlled room with food (pelleted rodent chow) and water available ad libitum. The compounds or vehicle (water) can be dosed once daily for 3 weeks (0.01–20 mg/kg, n=15 per group) by oral gavage. Body weight of each mouse can be measured daily and food intake per cage determined by weighing the amount of food left in the trough. At the end of the study, 24 h after giving the final dose of compound, the mice are weighed and then sacrificed by cervical dislocation. The epididymal fat pads from each mouse are excised and weighed. The fat versus body weight ratio is determined for each mouse using the absolute body weights and the fat pad weights.

A reduction in fat pad weight is indicative of a reduction in total body fat.

The present invention is illustrated by the following Examples. However, it should be understood that the invention is not limited to the specific details of these examples.

EXAMPLE 1

5-{2-[2-(3-Chloro-phenyl)-2(R)-hydroxy-ethylamino]-propyl}-1,3-dihydroindole-2,2-dicarboxylic acid dimethyl ester A. 2-Amino-5-bromobenzyl alcohol (1a): A solution of 12.316 g (0.1 mol) of 2-aminobenzyl alcohol in 300 mL of dry ether was treated at about 0° C. with 40.97 g (0.1 mol) of 2,4,4,6-tetrabromocyclohexa-2,5-dienone added in portions with vigorous stirring. Stirring was continued for about 1 hour at about 0° C., then the mixture was extracted twice with dilute HCl. The combined acid extracts were washed with ether and the ether was discarded. The acid solution was made alkaline with NaOH and extracted with fresh ether. The ether extracts were washed with water, then brine, dried ($Na_2SO_4$) and concentrated to afford 17.86 g (88%) of 1a, mp 107–110° C. $^1$H NMR ($CDCl_3$): d=7.22–7.17 (m, 2 H); 6.57 (d, 1 H); 4.61 (s, 2 H). (MS (El): m/z=201, 203 ($M^+$, Br isotopes).

B. N-(4-Bromo-2-hydroxymethylphenyl)-2,2,2-trifluoroacetamide (1b): A solution of 14.09 g (69.7 mmol) of 2-amino-5-bromobenzyl alcohol and 13.7 mL (97 mmol) of triethylamine in 240 mL of ether was cooled to about 0° C. A solution of 10.8 mL (76.7 mmol) of trifluoroacetic anhydride in 10 mL of ether was added dropwise, and the mixture was then stirred for about 1 hour at about 0° C. The mixture was then washed with dilute $H_2SO_4$, three times with water, dried ($MgSO_4$), and concentrated to afford an oil that was crystallized by adding hexanes and cooling in ice. Filtration gave 14.51 g (70%) of 1b, mp 97°–103° C. (softens 80° C.). $^1$H NMR ($CDCl_3$): d=10.02 (br, 1 H); 8.09 (d, 1 H); 7.50 (d of d, 1 H); 7.34 (d, 1 H); 4.81 (s, 2 H). MS (El): m/z=297, 299 ($M^+$, Br isotopes).

C. N-(4-Bromo-2-bromomethylphenyl)-2,2,2-trifluoroacetamide (1c): A solution of 14.51 g (48.7 mmol) of N-(4-bromo-2-hydroxymethylphenyl)-2,2,2-trifluoroacetamide in 110 mL of ether and 80 mL of dichloromethane was treated with 2.59 mL (27.25 mmol) of phosphorus tribromide at about 25° C. The mixture was stirred at about 25° C. for about 5 min, then heated under reflux for about 30 min. The reaction mixture was poured into a mixture of ether and ice water in a separatory funnel and shaken vigorously. The layers were separated and the organic phase was washed twice with water, then brine, dried ($Na_2SO_4$) and concentrated to give an oil that was crystallized by the addition of hexanes. The solid was filtered, washed with hexanes and dried to give 18.5 g (93%) of 1c, mp 133°–135° C. $^1$H NMR ($CDCl_3$): d=8.32 (br, 1 H); 7.79 (d, 1 H); 7.56 (d of d, 1 H); 7.54 (s, 1 H); 4.43 (s, 2 H).

D. 5-Bromo-1-trifluoroacetyl-1,3-dihydroindole-2,2-dicarboxylic acid diethyl ester (1d): A solution of 9.46 g (26.2 mmol) of N-(4-bromo-2-bromomethylphenyl)-2,2,2-trifluoroacetamide and 6.70 mL (39.31 mmol) of diethyl bromomalonate in 180 mL of THF was cooled to about 5° C. under nitrogen. With vigorous stirring, a solution of potassium tert-butoxide (65.5 mL, 65.5 mmol, 1M in THF) was added in a rapid stream from a syringe, maintaining the internal temperature below about 17° C. The mixture was stirred for about 45 min at about 10° C., then it was poured into a mixture of ethyl acetate and dilute HCl. The organic phase was separated, washed twice with water, then with brine, dried ($Na_2SO_4$), and concentrated to give an oil. This was chromatographed on silica gel (4:1 ethyl acetate—hexanes) to give 5.79 g (50%) of 1d as an oil. $^1$H NMR ($CDCl_3$): d=7.42–7.36 (m, 3 H); 4.29 (q, 4 H); 3.75 (br s, 2 H); 1.29 (t, 6 H). MS (El): m/z=437, 439 ($M^+$, Br isotopes).

E. 5-Bromo-1,3-dihydroindole-2,2-dicarboxylic acid dimethyl ester (1e): A solution of 3.14 g (7.17 mmol) of 5-bromo-1-trifluoroacetyl-1,3-dihydroindole-2,2-dicarboxylic acid diethyl ester and 0.581 g (10.75 mmol) of sodium methoxide was stirred in 15 mL of dry methanol under nitrogen at about 25° C. for about 1.5 hours. The reaction mixture was diluted with ethyl acetate and then added to a mixture of ethyl acetate and water. The organic phase was separated, washed twice with water, then with brine, dried (Na$_2$SO$_4$) and concentrated to a solid residue. This was dissolved in hot ethyl acetate and precipitated by the addition of hexanes to give 1.424 g (63%) of 1e, mp 113°–155° C. $^1$H NMR (CDCl$_3$): d=7.16–7.13 (m, 2 H); 6.58 (d, 1 H); 4.95 (br, 1 H); 3.78 (s, 6 H); 3.64 (s, 2 H). MS (El): m/z=313, 315 (M$^+$, Br isotopes).

F. 5-(2-Oxoproryl)-1,3-dihydroindole-2,2-dicarboxylic acid dimethyl ester (1f): A mixture of 0.238 mL (2.16 mmol) of isopropenyl acetate and 0.55 mL (1.91 mmol) of tri-n-butyltin methoxide in 5 mL of toluene was stirred under nitrogen for about 18 hours at about 25° C. The mixture was then treated with 0.400 g (1 mmol) of 5-bromo-1,3-dihydroindole-2,2-dicarboxylic acid dimethyl ester, 0.015 g (0.05 mmol) of palladium acetate, and 0.039 g (0.1 mmol) of tri-o-tolylphosphine and heated at about 90° C. for about 5 hours. The cooled reaction mixture was washed twice with water, brine, dried (Na$_2$SO$_4$), and concentrated to afford a dark oil. This was chromatographed on silica gel (24:1 dichloromethane—ethyl acetate) to give 0.265 g (71%) of 1f as an oil that crystallized on standing, mp 90°–95° C. $^1$H NMR (CDCl$_3$): d=6.87 (m, 2 H); 6.65 (d, 1 H); 4.97 (s, 1 H); 3.76 (s, 6 H); 3.64 (s, 2 H); 3.53 (s, 2 H); 2.09 (s, 3 H). MS (El): m/z=291 (M$^+$).

G. 5-{2-[2-(3-Chloro-phenyl)-2(R)-hydroxy-ethylamino]-propyl}-1,3-dihydroindole-2,2-dicarboxylic acid dimethyl ester (1g): A mixture of 0.0855 g (0.50 mmol) of (R)-2-amino-1-(3-chlorophenyl)ethanol and 0.146 g (0.50 mmol) of 5-(2-oxopropyl)-1,3-dihydroindole-2,2-dicarboxylic acid dimethyl ester in 3 mL of 1,2-dichloroethane was stirred at about 25° C. while sodium triacetoxyborohydride (0.159 g, 0.75 mmol) and acetic acid (0.043 mL, 0.75 mmol) were added. The mixture was stirred at about 25° C. for about 18 hours, after which the reaction mixture was treated with ethyl acetate and water. Dilute HCl was added to decompose any remaining borohydride species and the mixture was stirred for about 10 min. The aqueous phase was then made alkaline by the addition of sodium bicarbonate and the layers were separated. The organic phase was washed with water, brine, dried (Na$_2$SO$_4$) and concentrated. The residue was chromatographed on silica gel (23:2 dichloromethane—methanol) to afford 0.080 g (36%) of 1g as a foam. $^1$H NMR (CDCl$_3$): d=7.39 (m, 1 H); 7.23 (m, 3 H); 6.83 (m, 2 H); 6.60 (m, 1 H); 4.94 (d, 1 H); 4.61 (m, 1 H); 3.78 (s, 6 H); 3.62 (d, 2 H); 3.07–2.84 (m, 4 H); 2.62 (m, 3 H); 1.06 (d, 3 H). MS (NH$_3$ Cl): m/z=447, 449 (M+ H+, Cl isotopes).

EXAMPLE 2

1-Benzenesulfonyl-5-{2-[2-(3-chloro-phenyl)-2(R)-hydrox3-ethylamino]-propyl}-1,3-dihydroindole-2,2-dicarboxylic acid dimethyl ester A. 1-Benzenesulfonyl-5-bromo-1,3-dihydroindole-2,2-dicarboxylic acid dimethyl ester (2a): A solution of 0.307 g (0.98 mmol) of 5-bromo-1,3-dihydroindole-2,2-dicarboxylic acid dimethyl ester (1e) in 5 mL of dry THF was cooled to about –70° C. under nitrogen and treated with lithium bis(trimethylsilyl)amide (LiN(SiMe$_3$)$_2$)(1.08 mL, 1.08 mmol, 1M in THF). The mixture was stirred for about 5 min at about –70° C., then was stirred for about 10 min at about –10° C. Benzenesulfonyl chloride (0.138 mL, 1.08 mmol) was added in one portion and the mixture was stirred for about 2.5 hours at about –10° C. The mixture was then poured into ethyl acetate and dilute H$_3$PO$_4$ and the organic phase was separated, washed twice with water, brine, dried (Na$_2$SO$_4$), and evaporated. The residue was chromatographed on silica gel (dichloromethane) to give 0.410 g (92%) of 2a as a colorless oil. $^1$H NMR (CDCl$_3$): d=8.10 (m, 2 H); 7.60–7.46 (m, 3 H); 7.22–7.16 (m, 2 H); 6.93 (d, 1 H); 3.88 (s, 6 H); 3.77 (s, 2 H). MS (El): m/z=453, 455 (M$^+$, Br isotopes).

B. 1-Benzenesulfonyl-5-(2-oxopropyl)-1,3-dihydroindole-2,2-dicarboxylic acid dimethyl ester (2b): Prepared according to the procedure given for 1f from 0.168 mL (1.52 mmol) of isopropenyl acetate, 0.385 mL (1.34 mmol) of tri-n-butyltin methoxide, 0.010 g (0.045 mmol) of palladium acetate, 0.027 g (0.089 mmol) of tri-o-tolylphosphine, and 0.405 g (0.891 mmol) of 1-benzenesulfonyl-5-bromo-1,3-dihydroindole-2,2-dicarboxylic acid dimethyl ester (2a) in 4.5 mL of toluene; yield of 2b=0.310 g (81%). $^1$H NMR (CDCl$_3$): d=8.12 (d, 2 H); 7.49 (m, 3 H); 6.97 (d, 1 H); 6.90 (m, 1 H); 6.87 (d, 1 H); 3.88 (s, 6 H); 3.77 (s, 2 H); 3.57 (s, 2 H); 2.11 (s, 3 H). MS (El): m/z=431 (M$^+$).

C. 1-Benzenesulfonyl-5-{2-[2-(3-chloro-phenyl)-2(R)-hydroxy-ethylamino]-propyl}-1,3-dihydroindole-2,2-dicarboxylic acid dimethyl ester (2c): Prepared according to the procedure given for 1 g from 0.123 g (0.72 mmol) of (R)-2-amino-1-(3-chlorophenyl)ethanol, 0.310 g (0.72 mmol) of 1-benzenesulfonyl-5-(2-oxopropyl)-1,3-dihydroindole-2,2-dicarboxylic acid dimethyl ester, 0.229 g (1.08 mmol) of sodium triacetoxyborohydride, and 0.062 mL (1.08 mmol) of acetic acid in 4 mL of 1,2-dichloroethane; yield of 2c=0.158 g (37%). $^1$H NMR (CDCl$_3$): d=8.12 (d, 2 H); 7.51 (m, 3 H); 7.32 (m, 1 H); 7.21 (m, 3 H); 6.96 (m, 1 H); 6.87 (m, 2 H); 4.58 (m, 1 H); 3.88 (s, 6 H); 3.76 (d, 2 H); 2.87 (m, 2 H); 2.61 (m, 5 H); 1.01 (d, 3 H). MS (NH$_3$Cl): m/z=587, 589 (M+ H$^+$, Cl isotopes).

EXAMPLE 3

1-Benzoyl-5-{2-[2-(3-chloro-phenyl)-2(R)-hydroxy-ethylamino]-propyl}-1,3-dihydroindole-2,2-dicarboxylic acid dimethyl ester A. 1-Benzoyl-5-bromo-1,3-dihydroindole-2,2-dicarboxylic acid dimethyl ester (3a): Prepared according to the procedure given for 2a from 0.105 g (0.33 mmol) of 5-bromo-1,3-dihydroindole-2,2-dicarboxylic acid dimethyl ester, 0.36 mL of 1M LiN(SiMe$_3$)$_2$, and 0.058 mL (0.5 mmol) of benzoyl chloride in 2 mL of THF; yield of 3a=140 g (100%). $^1$H NMR (CDCl$_3$): d=7.58–7.39 (m, 5 H); 7.23 (m, 1 H); 6.95 (d, 1 H); 5.82 (d, 1 H); 3.86 (s, 6 H); 3.73 (s, 2 H). MS (El): m/z=417, 419 (M$^+$, Br isotopes).

B. 1-Benzoyl-5-(2-oxopropyl)-1,3-dihydroindole-2,2-dicarboxylic acid dimethyl ester (3b): Prepared according to the procedure given for 1f from 0.250 mL (2.26 mmol) of isopropenyl acetate, 0.575 mL (2.0 mmol) of tri-n-butyltin methoxide, 0.015 g (0.067 mmol) of palladium acetate, 0.040 g (0.133 mmol) of tri-o-tolylphosphine, and 0.563 g (1.33 mmol) of 1-benzoyl-5-bromo-1,3-dihydroindole-2,2-dicarboxylic acid dimethyl ester in 6 mL of toluene; yield of 3b=0.337 g (64%). $^1$H NMR (CDCl$_3$): d=7.57–7.39 (m, 5 H); 6.96 (m, 1 H); 6.64 (d, 1 H); 5.87 (d, 1 H); 3.82 (s, 6 H); 3.69 (s, 2 H); 3.55 (s, 2 H); 2.11 (s, 3 H). MS (El): m/z=395 (M$^+$).

C. 1-Benzoyl-5-{2-[2-(3-chloro-phenyl)-2(R)-hydroxy-ethylamino]-propyl}-1,3-dihydroindole-2,2-dicarboxylic acid dimethyl ester (3c): Prepared according to the procedure given for 1g from 0.143 g (0.836 mmol) of (R)-2-amino-1-(3-chlorophenyl)ethanol, 0.330 g (0.836 mmol) of 1-benzoyl-5-(2-oxopropyl)-1,3-dihydroindole-2,2-dicarboxylic acid dimethyl ester, 0.265 g (1.25 mmol) of sodium triacetoxyborohydride, and 0.071 mL (1.25 mmol) of acetic acid in 4 mL of 1,2-dichloroethane; yield of 3c=0.173 g (37%). $^1$H NMR (CDCl$_3$): d=7.57–7.40 (m, 5 H); 7.31 (m, 1 H); 7.23–7.16 (m, 4 H); 6.91 (m, 1 H); 6.61 (m, 1 H); 5.86 (m, 1 H); 4.54 (m, 1 H); 3.83 (s, 6 H); 3.68 (d, 2 H); 2.96–2.44 (m, 6 H); 1.01 (d, 3 H). MS (NH$_3$ Cl): m/z=551, 553 (M+ H$^+$, Cl isotopes).

EXAMPLE 4

1-Benzyl-5-{2-[2-(3-chloro-phenyl)-2(R)-hydroxy-ethylamino]-propyl}-1,3-dihydroindole-2,2-dicarboxylic acid dimethyl ester A. 1-Benzyl-5-bromo-1,3-dihydroindole-2,2-dicarboxylic acid dimethyl ester (4a): Prepared according to the procedure given for 2a from 0.314 g (1 mmol) of 5-bromo-1,3-dihydroindole-2,2-dicarboxylic acid dimethyl ester, 1.1 mL of 1M LiN(SiMe$_3$)$_2$, 0.238 mL (2 mmol) of benzyl bromide, and 0.150 g (1 mmol) of sodium iodide in 4 mL of THF and 4 mL of DMF; yield of 4a=0.222 g (55%). $^1$H NMR (CDCl$_3$): d=7.27–7.21 (m, 5 H); 7.13 (m, 1 H); 6.95 (d, 1 H); 6.02 (d, 1 H); 4.59 (s, 2 H); 3.71 (s, 2 H); 3.66 (s, 6 H). MS (El): m/z=403, 405 (M$^+$, Br isotopes).

B. 1-Benzyl-5-(2-oxopropyl)-1,3-dihydroindole-2,2-dicarboxylic acid dimethyl ester (4b): Prepared according to the procedure given for 1f from 0.187 mL (1.36 mmol) of isopropenyl acetate, 0.346 mL (1.20 mmol) of tri-n-butyltin methoxide, 0.010 g (0.045 mmol) of palladium acetate, 0.024 g (0.079 mmol) of tri-o-tolylphosphine, and 0.322 g (0.80 mmol) of 1-benzyl-5-bromo-1,3-dihydroindole-2,2-dicarboxylic acid dimethyl ester in 5 mL of toluene; yield of 4b=0.241 g (50%). $^1$H NMR (CDCl$_3$): d=7.25 (m, 5 H); 6.88 (m, 1 H); 6.77 (d, 1 H); 6.13 (d, 1 H); 4.61 (s, 2 H); 3.71 (s, 2 H); 3.65 (s, 6 H); 3.51 (s, 2 H); 2.09 (s, 3 H). MS (El): m/z=381 (M$^+$).

C. 1-Benzyl-5-{2-[2-(3-chloro-phenyl)-2(R)-hydroxy-ethylamino]-propyl}-1,3-dihydroindole-2,2-dicarboxylic acid dimethyl ester (4c): Prepared according to the procedure given for 1g from 0.108 g (0.633 mmol) of (R)-2-amino-1-(3-chlorophenyl)ethanol, 0.241 g (0.633 mmol) of 1-benzyl-5-(2-oxopropyl)-1,3-dihydroindole-2,2-dicarboxylic acid dimethyl ester, 0.212 g (0.95 mmol) of sodium triacetoxyborohydride, and 0.057 mL (0.95 mmol) of acetic acid in 4 mL of 1,2-dichloroethane; yield of 4c=0.136 g (40%). $^1$H NMR (CDCl$_3$): d=7.33 (m, 1 H); 7.28–7.15 (m, 9 H); 6.83 (d, 1 H); 6.71 (m, 1 H); 6.08 (m, 1 H); 4.60 (s, 2 H); 4.58 (m, 1 H); 3.69 (d, 2 H); 3.66 (s, 6 H); 2.81–2.79 (m, 4 H); 2.55 (m, 2 H); 1.03 (d, 3 H). MS (NH$_3$ Cl): m/z=537, 539 (M+ H+, Cl isotopes).

EXAMPLE 5

1-Acetyl-5-{2-[2-(3-chloro-phenyl)-2(R)-hydroxy-ethylamino]-propyl}-1,3-dihydroindole-2,2-dicarboxylic acid dimethyl ester A. 1-Acetyl-5-bromo-1,3-dihydroindole-2,2-dicarboxylic acid dimethyl ester (5a): Prepared according to the procedure given for 2a from 0.314 g (1 mmol) of 5-bromo-1,3-dihydroindole-2,2-dicarboxylic acid dimethyl ester, 1.1 mL of 1M LiN(SiMe$_3$)$_2$, and 0.078 mL (1.1 mmol) of acetyl chloride in 4 mL of THF; yield of 5a=0.337 g (95%). $^1$H NMR (CDCl$_3$): d=7.36–7.25 (m, 3 H); 3.80 (s, 6 H); 3.78 (s, 2 H); 2.45 (br s, 3 H). MS (El): m/z=355, 357 (M$^+$, Br isotopes).

B. 1-Acetyl-5-(2-oxopropyl)-1,3-dihydroindole-2,2-dicarboxylic acid dimethyl ester (5b): Prepared according to the procedure given for 1f from 0.177 mL (1.61 mmol) of isopropenyl acetate, 0.410 mL (1.42 mmol) of tri-n-butyltin methoxide, 0.011 g (0.049 mmol) of palladium acetate, 0.029 g (0.095 mmol) of tri-o-tolylphosphine, and 0.337 g (0.95 mmol) of 1-acetyl-5-bromo-1,3-dihydroindole-2,2-dicarboxylic acid dimethyl ester in 5 mL of toluene; yield of 5b=0.254 g (80%). $^1$H NMR (CDCl$_3$): d=7.12 (m, 1 H); 7.03 (m, 2 H); 3.79 (s, 6 H); 3.65 (br s, 4 H); 2.47 (br s, 3 H); 2.17 (s, 3 H). MS (El): m/z=333 (M$^+$).

C. 1-Acetyl-5-{2-[2-(3-chloro-phenyl)-2(R)-hydroxy-ethylamino]-propyl}-1,3-dihydroindole-2,2-dicarboxylic acid dimethyl ester (5c): Prepared according to the procedure given for 1g from 0.131 g (0.763 mmol) of (R)-2-amino-1-(3-chlorophenyl)ethanol, 0.254 g (0.763 mmol) of 1-acetyl-5-(2-oxopropyl)-1,3-dihydroindole-2,2-dicarboxylic acid dimethyl ester, 0.243 g (1.15 mmol) of sodium triacetoxyborohydride, and 0.066 mL (1.15 mmol) of acetic acid in 5 mL of 1,2-dichloroethane; yield of 5c=0.125 g (33%). $^1$H NMR (CDCl$_3$): d=7.34 (m, 1 H); 7.24 (m, 3 H); 7.02 (m, 1 H); 6.98 (m, 2 H); 4.62 (m, 1 H); 3.80 (s, 6 H); 3.63 (br, 2 H); 2.88 (m, 2 H); 2.58 (m, 3 H); 2.48 (br, 3 H); 1.07 (d, 3 H). MS (NH$_3$ Cl): m/z=489, 491 (M+ H$^+$, Cl isotopes).

EXAMPLE 6

5-{2-[2-(3-Chloro-phenyl)-2(R)-hydroxy-ethylamino]-propyl}-1-phenylacetyl-1,3-dihydro-indole-2,2-dicarboxylic acid dimethyl ester A. 5-Bromo-1-phenylacetyl-1,3-dihydroindole-2,2-dicarboxylic acid dimethyl ester (6a): Prepared according to the procedure given for 2a from 0.314 g (1 mmol) of 5-bromo-1,3-dihydroindole-2,2-dicarboxylic acid dimethyl ester, 1.1 mL of 1M LiN(SiMe$_3$)$_2$, and 0.145 mL (1.1 mmol) of phenylacetyl chloride in 4 mL THF; yield of 6a=0.234 g (54%). $^1$H NMR (CDCl$_3$): d=7.35–7.23 (m, 8 H); 4.02 (br, 2 H); 3.78 (s, 6 H); 3.68 (s, 2 H). MS (El): m/z=431,433 (M$^+$, Br isotopes).

B. 1-Phenylacetyl-5-(2-oxopropyl)-1,3-dihydroindole-2,2-dicarboxylic acid dimethyl ester (6b): Prepared according to the procedure given for 1f from 0.101 mL (0.921 mmol) of isopropenyl acetate, 0.234 mL (0.813 mmol) of tri-n-butyltin methoxide, 0.011 g (0.049 mmol) of palladium acetate, 0.030 g (0.099 mmol) of tri-o-tolylphosphine, and 0.234 g (0.54 mmol) of 5-bromo-1-phenylacetyl-1,3-dihydroindole-2,2-dicarboxylic acid dimethyl ester in 1 mL of toluene; yield of 6b=0.164 g (74%). $^1$H NMR (CDCl$_3$): d=7.32 (m, 5 H); 7.25 (m, 1 H); 7.01 (m, 2 H); 4.08 (br, 2 H); 3.78 (s, 6 H); 3.68 (br, 2 H); 3.63 (s, 2 H); 2.16 (s, 3 H). MS (El): m/z=409 (M$^+$).

C. 5-{2-[2-(3-Chloro-phenyl)-2(R)-hydroxy-ethylamino]-propyl}-1-phenylacetyl-1,3-dihydro-indole-2,2-dicarboxylic acid dimethyl ester (6c): Prepared according to the procedure given for 1g from 0.0686 g (0.40 mmol) of (R)-2-amino-1-(3-chlorophenyl)ethanol, 0.164 g (0.4 mmol) of 1-phenylacetyl-5-(2-oxopropyl)-1,3-dihydroindole-2,2-dicarboxylic acid dimethyl ester, 0.127 g (0.60 mmol) of sodium triacetoxyborohydride, and 0.034 mL (0.60 mmol) of acetic acid in 3 mL of 1,2-dichloroethane; yield of 6c=0.051 g (22%). $^1$H NMR (CDCl$_3$): d=7.33 (m, 5 H); 7.22 (m, 4 H); 6.95 (m, 3 H); 4.61 (m, 1 H); 4.09 (br, 2 H); 3.79 (s, 6 H); 3.75 (br, 2 H); 2.86 (m, 2 H); 2.69–2.56 (m, 3 H); 1.05 (d, 3 H). MS (NH$_3$ Cl): m/z=565, 567 (M+H$^+$, Cl isotopes).

EXAMPLE 7

5-{2-[2-(3-Chloro-phenyl)-2(R)-hydroxy-ethylamino]-propyl}-1-ethyl-1,3-dihydroindole-2,2-dicarboxylic acid dimethyl ester:

A. 5-Bromo-1-ethyl-1,3-dihydroindole-2,2-dicarboxylic acid dimethyl ester (7a): Prepared according to the procedure given for 2a from 0.314 g (1 mmol) of 5-bromo-1,3-dihydroindole-2,2-dicarboxylic acid dimethyl ester, 1.1 mL of 1M LiN(SiMe$_3$)$_2$, and 0.335 mL (5 mmol) of ethyl iodide in 3 mL of THF and 3 mL of DMF; yield of 7a=0.095 g (33%). $^1$H NMR (CDCl$_3$): d=7,18 (d, 1 H); 7.10 (m, 1 H); 6.31 (d, 1 H); 3.78 (s, 6 H); 3.58 (s, 2 H); 3.38 (q, 2 H); 1.14 (t, 3 H). MS (El): m/z=341, 343 (M$^+$, Br isotopes).

B. 1-Ethyl-5-(2-oxopropyl)-1,3-dihydroindole-2,2-dicarboxylic acid dimethyl ester (7b): Prepared according to the procedure given for 1f from 0.097 mL (0.884 mmol) of isopropenyl acetate, 0.224 mL (0.78 mmol) of tri-n-butyltin methoxide, 0.015 g (0.067 mmol) of palladium acetate, 0.040 g (0.131 mmol) of tri-o-tolylphosphine, and 0.178 g (0.52 mmol) of 5-bromo-1-ethyl-1,3-dihydroindole-2,2-dicarboxylic acid dimethyl ester in 4 mL of toluene; yield of 7b=0.104 g (62%). This material was used without further characterization.

C. 5-{2-[2-(3-Chloro-phenyl)-2(R)-hydroxy-ethylamino]-propyl}-1-ethyl-1,3-dihydroindole-2,2-dicarboxylic acid dimethyl ester (7c): Prepared according to the procedure given for 1g from 0.056 g (0.326 mmol) of (R)-2-amino-1-(3-chlorophenyl)ethanol, 0.104 g (0.326 mmol) of 1-ethyl-5-(2-oxopropyl)-1,3-dihydroindole-2,2-dicarboxylic acid dimethyl ester, 0.104 g (0.49 mmol) of sodium triacetoxyborohydride, and 0.028 mL (0.49 mmol) of acetic acid in 3 mL of 1,2-dichloroethane; yield of 7c=0.051 g (33%). $^1$H NMR (CDCl$_3$): d=7.36 (m, 1 H); 7.21 (m, 3 H); 6.81 (m, 2 H); 6.35 (m, 1 H); 4.69 (m, 1 H); 3.77 (s, 6 H); 3.56 (d, 2 H) 3.39 (q, 2 H); 2.87 (m, 2 H); 2.64 (m, 3 H); 1.15 (d, 3 H); 1.08 (t, 3 H). MS (NH$_3$ Cl): m/z=475, 477 (M+ H+, Cl isotopes).

EXAMPLE 8

5-{2-[2-(3-Chloro-phenyl)-2(R)-hydroxy-ethylamino]-propyl}-1-methyl-1,3-dihydroindole-2,2-dicarboxylic acid dimethyl ester:

A. 5-Bromo-1-methyl-1,3-dihydroindole-2,2-dicarboxylic acid dimethyl ester (8a): Prepared according to the procedure given for 2a from 0.314 g (1 mmol) of 5-bromo-1,3-dihydroindole-2,2-dicarboxylic acid dimethyl ester, 1.1 mL of 1M LiN(SiMe$_3$)$_2$, and 0.125 mL (2 mmol) of methyl iodide in 3 mL of THF; yield of 8a=0.134 g (41%). $^1$H NMR (CDCl$_3$): d=7.16 (d, 1 H); 7.07 (m, 1 H); 6.24 (d, 1 H); 3.76 (s, 6 H); 3.55 (s, 2 H); 2.91 (s, 3 H). MS (El): m/z=327, 329 (M$^+$, Br isotopes).

B. 1-Methyl-5-(2-oxopropyl)-1,3-dihydroindole-2 2-dicarboxylic acid dimethyl ester (8b): Prepared according to the procedure given for 1f from 0.15 mL (1.36 mmol) of isopropenyl acetate, 0.342 mL (1.20 mmol) of tri-n-butyltin methoxide, 0.015 g (0.067 mmol) of palladium acetate, 0.040 g (0.131 mmol) of tri-o-tolylphosphine, and 0.260 g (0.793 mmol) of 5-bromo-1-methyl-1,3-dihydroindole-2,2-dicarboxylic acid dimethyl ester in 4 mL of toluene; yield of 8b=0.291 g (79%). $^1$H NMR (CDCl$_3$): d=6.91 (d, 1 H); 6.85 (m, 1 H); 6.35 (d, 1 H); 3.77 (s, 6 H); 3.58 (s, 2 H); 3.54 (s, 2 H); 2.95 (s, 3 H); 2.10 (s, 3 H). MS (El): m/z=305 (M$^+$).

C. 5-{2-[2-(3-Chloro-phenyl)-2(R)-hydroxy-ethylamino]-propyl}-1-methyl-1,3-dihydroindole-2,2-dicarboxylic acid dimethyl ester (8c): Prepared according to the procedure given for 1g from 0.086 g (0.50 mmol) of (R)-2-amino-1-(3-chlorophenyl)ethanol, 0.152 g (0.50 mmol) of 1-methyl-5-(2-oxopropyl)-1,3-dihydroindole-2,2-dicarboxylic acid dimethyl ester, 0.159 g (0.75 mmol) of sodium triacetoxyborohydride, and 0.043 mL (0.75 mmol) of acetic acid in 4 mL of 1,2-dichloroethane; yield of 8c=0.075 g (32%). $^1$H NMR (CDCl$_3$): d=7.35 (m, 1 H); 7.22 (m, 3 H); 6.82 (m, 2 H); 6.32 (m, 1 H); 4.73 (m, 1 H); 3.78 (s, 6 H); 3.57 (d, 2 H); 2.96 (m, 2 H); 2.94 (s, 3 H); 2.61 (m, 3 H); 1.14 (d, 3 H). MS (NH$_3$ Cl): m/z=461, 463 (M+ H+, Cl isotopes).

EXAMPLE 9

1-Benzoyl-5-{2-[2-(3-chloro-phenyl)-2-hydroxy-ethylamino]-propyl}-2,3-dihydro-1H-indole-2-carboxylic acid methyl ester A. 2,3-Dihydro-1H-indole-2-carboxylic acid methyl ester (9a): Magnesium turnings (2.91 g, 120 mmol) were treated with 12 mL of methanol and heated until a brisk evolution of hydrogen set in, at which point a solution of 11.34 g (60 mmol) of 1H-indole-2-carboxylic acid ethyl ester in 50 mL of hot methanol was added, followed by 100 mL of methanol. The reaction flask was immediately cooled with an ice bath to about 35° C. When the evolution of hydrogen slowed, 1.00 g (41 mmol) of additional magnesium turnings were added. When the evolution of hydrogen slowed again, the reaction mixture was concentrated to about one-third the original volume and acidified with dilute HCl. The mixture was buffered by the addition of dilute ammonium hydroxide and extracted three times with ether. The combined ethereal extracts were washed with water, brine, dried (MgSO$_4$) and distilled in vacuo to give 9.157 g (86%) of 9a as a colorless oil. $^1$H NMR (CDCl$_3$): d=7.06 (m, 2 H); 6.73 (m, 2 H); 4.40 (d of d, 1 H); 3.75 (s, 3 H); 3.35 (m, 2 H). MS (El): m/z=177 (M$^+$).

B. 5-Bromo-2,3-dihydro-1H-indole-2-carboxylic acid methyl ester (9b): A solution of 9.157 g (51.7 mmol) of 2,3-dihydro-1H-indole-2-carboxylic acid methyl ester in 130 mL of dichloromethane was treated at about 0° C. with 21.2 g (51.7 mmol) of 2,4,4,6-tetrabromocyclohexa-2,5-dienone added in portions with vigorous stirring. Stirring was continued for about 1 hour at about 0° C., after which the mixture was washed with 2M sodium hydroxide, brine, dried (Na$_2$SO$_4$) and concentrated to give an oil (9.7 g, 73%). MS (El): m/z=255, 257 (M$^+$, Br isotopes). The oil was dissolved in 50 mL of hot ethyl acetate and treated with a hot solution of 7.25 g (37.9 mmol) of p-toluenesulfonic acid monohydrate in 50 mL of ethyl acetate. The precipitated crystals were filtered, washed with ethyl acetate and dried to give 8.78 g (40% overall) of the tosylate salt of 9b, mp 143°–147° C. $^1$H NMR (dmso-d$_6$): d=7.49 (d, 2 H); 7.17–7.07 (m, 4 H); 6.54 (d, 1 H); 4.46 (m, 1 H); 3.66 (s, 3 H); 3.29 (d of d, 1 H); 3.09 (d of d, 1 H); 2.29 (s, 3 H).

C. 1-Benzoyl-5-bromo-2,3-dihydro-1H-indole-2-carboxylic acid methyl ester (9c): A mixture of 0.95 g (3.71 mmol) of 5-bromo-2,3-dihydro-1H-indole-2-carboxylic acid methyl ester in 20 mL of dichloromethane was treated with benzoyl chloride (0.64 g, 4.6 mmol) and triethylamine (0.94 g, 9.2 mmol). After 2 hours, the reaction mixture was washed with 1M sodium carbonate, water, brine, dried (Na$_2$SO$_4$) and concentrated. The residue was digested with hot 3:1 hexanes—ether and filtered to give 1.08 g (81%) of 9c, mp 168°–169° C. $^1$H NMR (CDCl$_3$): d=7.45 (m, 5 H); 7.27–7.12 (m, 3 H); 5.07 (m, 1 H); 3.68 (s, 3 H); 3.54 (d of d, 1 H); 3.13 (d of d, 1 H). MS (El): m/z=359, 361 (M$^+$, Br isotopes).

D. 1-Benzoyl-5-(2-oxo-propyl)-2,3-dihydro-1H-indole-2-carboxylic acid methyl ester (9d): Prepared according to the procedure given for 1f from 0.59 mL (5.4 mmol) of isopropenyl acetate, 1.28 mL (4.46 mmol) of tri-n-butyltin methoxide, 0.033 g (0.15 mmol) of palladium acetate, 0.090 g (0.30 mmol) of tri-o-tolylphosphine, and 1.07 g (3 mmol) of 1-benzoyl-5-bromo-2,3-dihydro-1H-indole-2-carboxylic acid methyl ester in 60 mL of toluene; yield of 9d=0.771 g (70%). $^1$H NMR (CDCl$_3$): d=7.48 (m, 5 H); 6.99 (m, 2 H); 6.70 (m, 1 H); 5.03 (m, 1 H); 3.69 (s, 3 H); 3.57 (s, 2 H); 3.52 (d of d, 1 H); 3.16 (d of d, 1 H); 2.12 (s, 3 H). MS (El): m/z=337 (M$^+$).

E. 1-Benzoyl-5-{2-[2-(3-chloro-phenyl)-2-hydroxy-ethylamino]-propyl}-2,3-dihydro-1 H-indole-2-carboxylic acid methyl ester (9e): Prepared according to the procedure given for 1g from 0.342 g (2 mmol) of (R)-2-amino-1-(3-chlorophenyl)ethanol, 0.68 g (2.0 mmol) of 1-benzoyl-5-(2-oxo-propyl)-2,3-dihydro-1H-indole-2-carboxylic acid methyl ester, 0.64 g (3.0 mmol) of sodium triacetoxyborohydride, and 0.17 mL (3 mmol) of acetic acid in 15 mL of 1,2-dichloroethane; yield of 9e=0.328 g (33%). $^1$H NMR (CDCl$_3$): d=7.57–7.40 (m, 5 H); 7.31 (m, 1 H); 7.23–7.16 (m, 4 H); 6.93 (m, 2 H); 5.08 (m, 1 H); 4.54 (m, 1 H); 3.69 (s, 3 H); 3.50 (d of d, 1 H); 3.12 (d of d, 1 H); 2.96–2.44 (m, 6 H); 1.01 (d, 3 H). MS (NH$_3$ Cl): m/z=493, 495 (M+ H+, Cl isotopes).

EXAMPLE 10

6-{2-[2-(3-Chloro-phenyl)-2-hydroxy-ethylamino]-propyl}-chroman-2,2-dicarboxylic acid diethyl ester A. 4-Bromo-2-(2-hydroxy-ethyl)-phenol (10a): A solution of borane-methyl sulfide complex (371 mL, 0.742 mol, 2M in THF) was added dropwise over about 1.5 hours to a solution of 143.0 g (0.619 mol) of 5-bromo-2-hydroxyphenylacetic acid in 1400 mL of dry THF, keeping the reaction temperature below about 30° C. The reaction mixture was stirred overnight at room temperature. Then, it was cooled to about 0° C., and 5M NaOH (706 mL) was added slowly with stirring, keeping the temperature below about 10° C. The reaction mixture was then was stirred in an ice bath for about 0.5 hour and at room temperature for about 2 hours. The THF was evaporated and the oily residue was diluted with 300 mL of water. A cold solution of 3M HCl was added slowly to pH 7, and the mixture was extracted three times with 300 mL of ethyl acetate. The combined organic layers were washed with water, brine, dried ($Na_2SO_4$) and concentrated to a light yellow oil. This was triturated in 300 mL hexanes and filtered to give 126.0 g (94%) of 10a as a tan solid, mp 63°–65° C. $^1$H NMR ($CDCl_3$): d=9.50 (s, 1 H); 7.16 (s, 1 H); 7.06 (d, 1H); 6.66 (d, 1 H); 4.63 (br, 1 H); 3.55 (t, 2 H); 2.62 (t, 2 H). MS (El): m/z=218 (M+1).

B. 2-[4-Bromo-2-(2-hydroxy-ethyl)-phenoxy]-malonic acid diethyl ester (10b): A solution of 109.0 g (0.502 mol) of 10a in 830 mL of dry DMF was added dropwise over about 1.5 hours to a suspension of 24.1 g (0.602 mol, 60% dispersion in mineral oil) of NaH in 300 mL anhydrous DMF. After addition, the reaction mixture was stirred for about 1 hour before 111.5 mL (0.653 mol) of diethyl bromomalonate was added dropwise over about 1 hour. The reaction mixture was then stirred at about 60° C. for about 18 hours. The reaction mixture was cooled to room temperature, diluted with 300 mL ethyl acetate, and poured over 300 mL of 0.5N HCl. The organic phase was separated, and the aqueous phase was extracted two more times with 100 mL portions of ethyl acetate. The combined organic phases were washed twice with water, then with brine, dried ($Na_2SO_4$), and concentrated to give an oil. This was chromatographed on silica gel (1:3 ethyl acetate-hexanes) to give 79.8 g (42%) of 10b as an oil. $^1$H NMR ($CDCl_3$): d=6.54 (s,1 H); 4.26 (q, 4H); 3.84 (t, 2H); 2.92 (t, 2H); 1.26 (t, 6H).

C. 6-Bromo-chroman-2,2-dicarboxylic acid diethyl ester (10c): A solution of 27.0 g (72 mmol) of the above compound in 400 mL of anhydrous dichloromethane was added 7.2 mL (93.6 mmol) of methanesulfonyl chloride dropwise at about 0° C. for about 0.5 hour. The reaction mixture was stirred for about 0.5 hour; then, 15 mL (108 mmol) of triethylamine was added dropwise at about 0° C. over about 0.5 hour. After addition, the reaction mixture was stirred at room temperature for about 16 hours and poured into 200 mL of 10% aqueous HCl. The organic phase was separated, and the aqueous phase was extracted two times with 100 mL dichloromethane. The combined organic phases were washed twice with water, then with brine, dried ($Na_2SO_4$), and concentrated to give 32.6 g (100%) of the intermediate methanesulfonate as an oil. $^1$H NMR ($CDCl_3$): d=7.22–7.32 (m, 2H); 6.58 (d, 1H); 4.5 (t, 2H); 4.26–4.30 (m, 4H); 3.12 (t, 2H); 2.9 (s, 3H); 1.26–1.32 (m, 6H). A solution of 20.0 g (44 mmol) of the above methanesulfonate in 600 mL of methyl ethyl ketone was treated with 6.7 g (48.5 mmol) of $K_2CO_3$. The mixture was heated to reflux with vigorous stirring for about 5 hours. The reaction mixture was then cooled to room temperature, and concentrated to a thick residue which was diluted with 300 mL ethyl -acetate, and poured into 300 mL of 10% aqueous HCl. The organic phase was separated, and the aqueous phase was extracted twice with 100 mL ethyl acetate.

The combined organic phases were washed twice with water, then with brine, dried ($Na_2SO_4$), and concentrated to give an oil. This was chromatographed on silica gel (1:3 ethyl acetate-hexanes) to give 6.4 g of 10c as an oil. $^1$H NMR ($CDCl_3$): d=7.10–7.18 (m, 2H); 6.83 (d, 1H); 4.24 (q, 4H); 2.69 (t, 2H); 2.38 (t, 2H); 1.18–1.24 (m, 6H). MS (El): m/z=358 (M+1).

D. 6-(2-Oxo-propyl)-chroman-2,2-dicarboxylic acid diethyl ester (10d): Prepared 25 according to the procedure given for 1f from 2.4 g (6.81 mmol) of 6-bromochroman-2,2-dicarboxylic acid diethyl ester, 3 mL (10.2 mmol) of tri-n-butyltin methoxide, 1.13 mL (10.2 mmol) of isopropenyl acetate, 76 mg (0.34 mmol) of palladium acetate, 207 mg (0.681 mmol) of tri-o-tolyl-phosphine in 15 mL anhydrous toluene; yield of 10d=750 mg (33%). $^1$H NMR ($CDCl_3$): d=6.88 (s, 2H); 6.78 (s, 1H); 4.18–4.23 (q, 4H); 3.50 (s, 2H); 2.68 (t,2H); 2.38 (t, 2H); 2.06 (s,3H); 1.22 (t, 6H). MS (El): m/z=334.

E. 6-{2-[2-(3-Chloro-phenyl)-2-hydroxy-ethylamino]-propyl}-chroman-2,2-dicarboxylic acid diethyl ester (10e): Prepared according to the procedure given for 1 g from 250 mg (0.748 mmol) of 6-(2-oxo-propyl)-chroman-2,2-dicarboxylic acid diethyl ester, 270 mg (0.748 mmol) of (R)-2-amino-1-(3-chlorophenyl)ethanol N-BOC alanine salt, 238 mg (1.12 mmol) of sodium triacetoxyborohydride in 8 mL of 1,2-dichloroethane; yield of 10e=300 mg (82%). $^1$H NMR ($CDCl_3$): d=7.32 (s, 1H); 7.16–7.24 (m, 3H); 6.90 (d, 2H); 6.77 (d, 1H); 4.50–4.61 (m, 1H); 4.20–4.28 (q, 4H); 2.76–2.96 (m, 3H); 2.68–2.72 (m, 2H); 2.50–2.64 (m, 3H); 2.39–2.45 (m, 2H); 1.22–1.26 (t, 6H); 1.03 (d, 3H). MS (FAB): m/z=491 (M+1).

EXAMPLE 11

5-{2-[2-(3-Chloro-phenyl)-2-hydroxy-ethylamino]-propyl}-3H-benzofuran-2,2-dicarboxylic acid diethyl ester A. 5-Bromo-3-hydroxy-3H-benzofuran-2,2-dicarboxylic acid diethyl ester (11a): A slurry of 10.0 g (50 mmol) of 5-bromosalicylaldehyde, 12.6 g (52.5 mmol) of diethyl bromomalonate, 6.9 g (50 mmol) of $K_2CO_3$ in 50 mL of methyl ethyl ketone was refluxed with stirring for about 4.5 hours. The reaction mixture was poured into ethyl acetate, washed with water, brine, dried ($Na_2SO_4$), and concentrated to give a light brown solid that was recrystallized from ethyl acetate:cyclohexane to give 8.75 g (48.6%) of 11a as colorless crystals. $^1$H NMR ($CDCl_3$): d=7.40 (s, 1H); 7.28 (d, 1H); 6.77 (d, 1H); 5.77 (d, 1H); 4.14–4.28 (m, 4H); 2.81 (d, 1H); 1.25 (q, 6H).

B. 5-Bromo-3H-benzofuran-2,2-dicarboxylic acid diethyl ester (11b): A mixture of 1.0 g (2.78 mmol) of the above product and 0.89 mL (5.57 mmol) of triethylsilane was heated to about 85° C. The reaction mixture then was diluted into ethyl acetate, washed twice with saturated $NaHCO_3$, then with brine, dried ($Na_2SO_4$), and concentrated to give 852 mg (89%) of 11b as an oil. $^1$H NMR ($CDCl_3$): d=7.19 (d, 2H); 6.72 (d, 1H); 4.24 (q, 4H); 2.65 (s, 2H); 1.23 (t, 6H).

C. 5-(2-Oxo-propyl)-3H-benzofuran-2,2-dicarboxylic acid diethyl ester (11c): Prepared according to the procedure given for 1f from 11.1 g (32.25 mmol) of 5-bromo-3H-benzofuran-2,2-dicarboxylic acid diethyl ester, 13.87 mL (48.38 mmol) of tri-n-butyltin methoxide, 5.33 mL (48.38 mmol) of isopropenyl acetate, 362 mg (1.61 mmol) of palladium acetate, 982 mg (3.22 mmol) of tri-o-tolylphosphine in 70 mL of anhydrous toluene; yield of 11c=4.01 g (38.7%) as an oil. $^1$H NMR ($CDCl_3$): d=6.90–6.96 (d, 2 H); 6.82 (d, 1 H); 4.20–4.26 (m, 4 H); 2.72 (s, 2 H); 2.56 (s, 2 H); 2.09 (s, 3 H); 1.24 (t, 6 H).

D. 5-(2-Amino-propyl)-3H-benzofuran-2,2-dicarboxylic acid diethyl ester (11d): A solution of 4.01 g (12.5 mmol) of 5-(2-oxo-propyl)-3H-benzofuran-2,2-dicarboxylic acid diethyl ester and 1.7 mL (12.5 mmol) of R-(+)-a-methyl-benzylamine in 16 mL of toluene was azeotroped at about 160° C. for about 20 hours, and was concentrated to an oil to give 5.29 g (100%) of the imine. $^1$H NMR (CDCl$_3$): d=7.12–7.26(m, 5 H); 6.97–7.00 (d, 2 H); 6.74–6.84 (d, 1 H); 4.34–4.60 (q, 1 H); 4.28–4.32 (q, 4 H); 3.68–3.76 (m, 3 H); 3.56 (d, 2 H); 1.66 (s, 1 H); 1.29 (d, 3 H); 1.28–1.32 (t, 6 H). A slurry of 5 mL Rainy-Ni (50% in water) was washed five times with 20 mL ethanol, then was added to a solution of 5.29 g (12.5 mmol) of the above imine in 20 mL of EtOH. The mixture was hydrogenated for about 80 hours, and was filtered through a celite pad. The greenish filtrate was then concentrated to the crude product which was chromatographed on silica gel (1:1 ethyl acetate: hexanes, then ethyl acetate, then 5:95 triethylamine-hexanes) to give 2.25 g (42.3%) of the amine as a brown oil. $^1$H NMR (CDCl$_3$): d=7.16–7.28 (m, 6H); 6.77 (d, 2H); 4.24 (q, 4H); 4.02–4.09 (m, 1H); 3.74–3.89 (m, 2H); 3.68 (s, 3H); 2.70–2.78 (m, 1H); 2.60–2.66 (q, 1H); 2.30–2.38 (q, 1H); 1.93 (s, 2 H); 1.26 (t, 6H); 0.84 (d, 3H). A solution of 705 mg of the above amine in 25 mL of EtOH was added to 350 mg of 10% Pd/C under nitrogen atmosphere, and was hydrogenated at 50 psi for about 22 hours. The reaction mixture then was filtered through a celite pad, and concentrated to 433 mg of the crude product as a pale beige-green oil which was chromatographed on silica gel (9:1 methanol-CHCl$_3$) to give 280 mg of 11d as a beige oil. H NMR (CDCl$_3$): d=6.95 (d, 2H); 6.83 (d, 1 H); 4.28 (q, 4H); 3.74 (s, 2H); 3.06 (br, 1H); 2.58–2.64 (q, 1H); 2.36–2.45 (q, 1 H); 1.58 (s, 2H); 1.28 (t, 6H); 1.07 (d, 3H). MS (El): m/z=321.

E. 5-{2-[2-(3-Chloro-phenyl)-2-hydroxy-ethylamino]-propyl}-3H-benzofuran-2,2-dicarboxylic acid diethyl ester (11e): A solution of 205 mg (0.0.64 mmol) of 5-(2-amino-propyl)-3H-benzofuran-2,2-dicarboxylic acid diethyl ester in 1.1 mL of anhydrous DMSO was treated with 109 mg (0.832 mmol) of N-(trimethylsilyl)acetamide, and the mixture was stirred for about 0.5 hour. (R)-3-Chlorostyrene oxide (108 mg, 0.704 mmol) was then added with stirring to produce a yellow solution which was heated to about 60° C. for about 48 hours, then cooled and stirred at room temperature for about 64 hours. The reaction mixture then was poured into 3 mL of cold 1N HCl, stirred for about 0.5 hour, adjusted to pH 11 with cold 6N NaOH, and extracted three times with ethyl acetate. The combined organic layers were washed with brine, dried (Na$_2$SO$_4$), and concentrated to 55 mg (18%) of the crude product as a beige oil. This was chromatographed on silica gel (5:95 methanol-CHCl$_3$) to give 34 mg (11%) of 11e. $^1$H NMR (CDCl$_3$): d=7.30 (s, 1H); 7.14–7.2 (m, 3H); 6.76–6.96 (m, 3H); 6.52–6.56 (br, 1 H); 4.50–4.56 (m, 1H); 4.24–4.30 (m, 4H); 3.73 (s, 2H); 2.82–2.88 (m, 2H); 2.54–2.65 (m, 4H); 1.28 (t, 6H); 1.02 (d, 3H).

EXAMPLE 12

1-Benzyl-6-{2-[2-(3-chloro-phenyl)-2-hydroxy-ethylamino]-propyl}-3,4-dihydro-1H-quinoline-2,2-dicarboxylic acid diethyl ester:

A. 2-[2-(2-Hydroxyethyl)-phenylamino]-malonic acid diethyl ester (12a): A mixture of 1.90 g (13.8 mmol) of 2-(2-aminophenyl)-ethanol and 1.65 9 (6.9 mmol) of diethyl bromomalonate was placed in a 100 mL round bottomed flask. The flask was left open and was placed in a vacuum oven at about 75° C. and ca. 50 torr for about 20 hours. The residue in the flask was triturated with ether repeatedly. The combined ethereal triturates were combined, filtered, and concentrated to afford an oil that was chromatographed on silica gel (2:1 hexanes—ethyl acetate) to give 1.30 g (64%) of 12a as an oil. $^1$H NMR (CDCl$_3$): d=7.14 (m, 2 H); 6.77 (t, 1 H); 6.56 (d, 1 H); 5.33 (d, 1 H); 4.80 (d, 1 H); 4.28 (q, 4 H); 3.94 (q, 2 H); 2.89 (t, 2 H); 1.95 (t, 1 H); 1.27 (t, 6 H). MS (El): m/z=295 (M$^+$).

B. 3,4-Dihydro-1H-quinoline-2,2-dicarboxylic acid diethyl ester (12b): A solution of 0.505 g (1.71 mmol) of 2-[2-(2-hydroxyethyl)-phenylamino]-malonic acid diethyl ester and 0.448 g (1.71 mmol) of triphenylphosphine in 8 mL of benzene was treated with 0.432 g (1.71 mmol) of 1,1'-(azodicarbonyl)dipiperidide. The mixture was stirred at about 20° C. for about 48 hours, after which the mixture was filtered and the filtrate was concentrated. Chromatography of the residue on silica gel (dichloromethane) afforded 0.289 g (61%) of 12b as a colorless oil. $^1$H NMR (CDCl$_3$): d=7.02 (m, 2 H); 6.69 (m, 2 H); 4.81 (s, 1 H); 4.23 (q, 4 H); 2.79 (t, 2 H); 2.36 (t, 2 H); 1.27 (t, 6 H). MS (El): m/z=277 (M$^+$).

C. 1-Benzyl-3,4-dihydro-1H-quinoline-2,2-dicarboxylic acid diethyl ester (12c): A solution of 2.18 g (7.87 mmol) of 3,4-dihydro-1H-quinoline-2,2-dicarboxylic acid diethyl ester in 40 mL of dry DMF was treated with 8.66 mL of a 1M solution of lithium bis(trimethylsilyl)amide in THF (8.66 mmol) at about –40° C. to about –50° C. The mixture was then allowed to come to about –10° C., at which point it was treated with 2.69 g (15.7 mmol) of benzyl bromide. The mixture was then stirred at about 0° C. for about 1 hour, after which it was allowed to warm to about 20° C. The reaction mixture was partitioned between water and ethyl acetate and the organic phase was washed with water, brine, dried (MgSO$_4$) and evaporated. The residue was chromatographed on silica gel (9:1 hexanes—ether) to afford 1.30 g (45%) of 12c as a solid. $^1$H NMR (CDCl$_3$): d=7.29 (m, 5 H); 6.96 (m, 2 H); 6.66 (m, 1 H); 6.48 (m, 1 H); 4.70 (s, 2 H); 4.05 (q, 4 H); 2.74 (t, 2 H); 2.63 (t, 3 H); 1.14 (t, 6 H). MS (El): m/z=367 (M$^+$).

D. 1-Benzyl-6-bromo-3,4-dihydro-1H-quinoline-2,2-dicarboxylic acid diethyl ester (12d): A solution of 1.30 g (3.54 mmol) of 1-benzyl-3,4-dihydro-1H-quinoline-2,2-dicarboxylic acid diethyl ester in 35 mL of dichloromethane was treated at about 0° C. with 1.45 g (3.54 mmol) of 2,4,4,6-tetrabromocyclohexa-2,5-dienone added in portions with vigorous stirring. Stirring was continued for about 1 hour at about 0° C., after which another 0.60 g (1.46 mmol) of 2,4,4,6-tetrabromocyclohexa-2,5-dienone was added. The mixture was then diluted with 250 mL of ethyl acetate and washed with 1M sodium hydroxide, brine, dried (Na$_2$SO$_4$) and concentrated. The residue was chromatographed on silica gel (2:1 hexanes—dichloromethane) to afford, after concentration of the fractions to a small volume and filtration of the resulting solid, 1.02 g (65%) of 12d as a white solid, mp 116°–117° C. An additional 0.335 g (21%) of 12d was obtained by concentration of the mother liquors. $^1$H NMR (CDCl$_3$): d=7.29 (m, 5 H); 7.11 (m, 1 H); 7.04 (m, 1 H); 6.36 (d, 1 H); 4.63 (s, 2 H); 4.10 (q, 4 H); 2.73 (t, 2 H); 2.48 (t, 2 H); 1.10 (t, 6 H). MS (NH$_3$ Cl): m/z=446, 448 (M+H+, Br isotopes).

E. 1-Benzyl-6-(2-oxo-propyl)-3,4-dihydro-1H-quinoline-2,2-dicarboxylic acid diethyl ester (12e): Prepared according to the procedure given for 1f from 0.36 mL (0.323 mmol) of isopropenyl acetate, 0.93 mL (3.23 mmol) of tri-n-butyltin methoxide, 0.005 9 (0.022 mmol) of palladium acetate, 0.013 g (0.043 mmol) of tri-o-tolylphosphine, and 0.96 g (2.15 mmol) of 1-benzyl-6-bromo-3,4-dihydro-1H-quinoline-2,2-dicarboxylic acid diethyl ester in 6 mL of toluene; yield of 12e=0.629 g (69%). $^1$H NMR (CDCl$_3$): d=7.29 (m, 5 H); 6.81 (m, 2 H); 6.40 (m, 1 H); 4.69 (s, 2 H); 4.08 (q, 4 H); 3.50 (s, 2 H); 2.72 (t, 2 H); 2.62 (t, 2 H); 2.11 (s, 3 H); 1.13 (t, 6 H). MS (El): m/z=423 (M$^+$).

F. 1-Benzyl-6-{2-[2-(3-chloro-phenyl)-2-hydroxy-ethylamino]-propyl}-3,4-dihydro-1H-quinoline-2,2-dicarboxylic acid diethyl ester (12f): Prepared according to the procedure given for 1g from 0.045 g (0.263 mmol) of (R)-2-amino-1-(3-chlorophenyl)ethanol, 0.111 g (0.263 mmol) of 1-benzyl-6-(2-oxo-propyl)-3,4-dihydro-1H-quinoline-2,2-dicarboxylic acid diethyl ester, 0.085 g (0.40 mmol) of sodium triacetoxyborohydride, and 0.022 mL (0.40 mmol) of acetic acid in 2 mL of 1,2-dichloroethane; yield of 12f=0.061 g (40%). $^1$H NMR (CDCl$_3$): 7.35 (m, 1 H); 7.27 (m, 8 H); 6.74 (m, 2 H); 6.39 (m, 1 H); 4.67 (s, 2 H); 4.56 (m, 1 H); 4.07 (m, 4 H); 2.96–2.43 (m, 11 H); 1.13 (t, 6 H); 1.04 (d, 3 H). MS (El): m/z=577 (MH$^+$).

EXAMPLE 13

1-Benzyl-5-{2-[2-(3-chloro-phenyl)-2-hydroxy-ethylamino]-propyl}-2,3-dihydro-1H-indole-2-carboxylic acid methyl ester A. 1-Benzyl-5-bromo-1H-indole-2-carboxylic acid ethyl ester (13a): A solution of 10.0 g (35.4 mmol) of 5-bromoindole-2-carboxylic acid ethyl ester in 70 mL of anhydrous DMSO was added to a suspension of 1.56 g (35.4 mmol) of sodium hydride (60% dispersion in mineral oil) in 40 ml of DMSO over about 1 hour. After addition, the solution was stirred at room temperature for about 1 hour before 4.1 mL (35.4 mmol) of benzyl chloride was added dropwise over about 15 minutes. The reaction mixture was then stirred at room temperature overnight. It was poured into 300 mL of water and extracted three times with 200 mL of toluene. The combined organic layers were washed twice with 200 mL of 5% aqueous HCl, then with brine, dried (Na$_2$SO$_4$), and concentrated to a light green oil. This was triturated with 20 mL of hexane and allowed to crystallize in a refrigerator. Filtration gave 12.70 g (100%) of 13a as a low melting solid. $^1$H NMR (CDCl$_3$): d=7.77 (s, 1H); 7.14–7.32 (m, 6H); 6.96 (d, 2H); 5.78 (s, 2H); 4.24–4.32 (q, 2H); 1.30–1.35 (t, 3H).

B. 1-Benzyl-5-bromo-2,3-dihydro-1 H-indole-2-carboxylic acid methyl ester (13b): A slurry of 2.0 g (5.58 mmol) of 1-benzyl-5-bromo-1H-indole-2-carboxylic acid ethyl ester in 28 mL of anhydrous methanol was treated with 0.41 g (16.7 mmol) of crushed Mg turnings and a few crystals of iodine. The reaction mixture was stirred at room temperature for about 5.5 hours. The reaction was poured into 50 mL of 1N HCl, and was stirred for about 5 min. The pH was then adjusted to pH 10 by adding 1N NaOH, and the mixture was extracted twice with 250 mL of ethyl acetate. The combined organic extracts were washed with brine, dried (Na$_2$SO$_4$), and concentrated to 1.70 g of the crude product as a dark oil. This was chromatographed on silica gel (5:95 ethyl acetate-hexane) to give 1.03 g (45%) of 13b as a yellow oil. $^1$H NMR (CDCl$_3$): d=7.20–7.26 (m, 5 H); 7.04–7.08 (d, 2 H); 6.23–6.26 (d, 1 H); 4.42–4.48 (d, 1 H); 4.18–4.25 (m, 2 H); 3.65 (d, 3 H); 3.26–3.36 (q, 1 H); 3.07–3.16 (q, 1 H).

C. 1-Benzyl-5-(2-oxo-propyl)-2,3-dihydro-1H-indole-2-carboxylic acid methyl ester (13c): Prepared according to the procedure given for 1f from 1.15 g (3.32 mmol) of 1-benzyl-5-bromo-2,3-dihydro-1H-indole-2-carboxylic acid methyl ester, 1.43 mL (4.98 mmol) of tri-n-butyltin methoxide, 0.55 mL (4.98 mmol) of isopropenyl acetate, 37 mg (0.17 mmol) of palladium acetate 101 mg (0.33 mmol) of tri-o-tolylphosphine in 3 mL of toluene; yield of 13c=741 mg (69%). $^1$H NMR (CDCl$_3$): d=7.20–7.28 (m, 5 H); 6.79–6.84 (t, 2 H); 6.32 –6.36 (d, 1 H); 4.42–4.46 (d, 1 H); 4.18–4.28 (m, 2 H); 3.63 (s, 3 H); 3.52 (s, 2 H); 3.28–3.36 (q, 1 H); 3.08–3.16 (q, 1 H); 2.08 (s, 3 H).

D. 1-Benzyl-5-{2-[2-(3-chloro-phenyl)-2-hydroxy-ethylamino]-propyl}-2,3-dihydro-1H-indole-2-carboxylic acid methyl ester (13d): A suspension of 730 mg (2.26 mmol) of 1-benzyl-5-(2-oxo-propyl)-2,3-dihydro-1H-indole-2-carboxylic acid methyl ester and 426 mg (2.48 mmol) of (R)-2-amino-1-(3-chlorophenyl)ethanol in 10 mL of toluene was azeotroped for 4 hours, then concentrated to an oil to give the imine. This imine was dissolved immediately in 15 mL of methanol, and was cooled in an ice bath. The cool solution was then treated with 84 mg (2.26 mmol) of sodium borohydride over about a 5 minute period. The ice bath was removed, and the reaction solution was stirred at room temperature for about 1 hour. The reaction was diluted with ethyl acetate, washed with water, then brine, dried (Na$_2$SO$_4$), and concentrated to an oil. This was chromatographed on silica gel (5:95 methanol-ethyl acetate to 10:90 methanol-ethyl acetate) to give 630 mg (58%) of 13d as an oil. $^1$H NMR (CDCl$_3$): d=7.17–7.30 (m, 9 H); 6.72–6.80 (q, 2 H); 6.18–6.25 (q, 1 H); 4.44–4.61 (m, 1 H); 4.38–4.43 (d, 1 H); 4.15–4.25 (m, 2 H); 3.62 (s, 3 H); 3.23–3.36 (m, 1 H); 3.04–3.16 (m, 1 H); 2.98 (d, 1 H); 2.96 (d, 1 H); 2.76–2.86 (m, 2 H); 2.20 (br, 2 H); 1.04 (m, 3 H).

We claim:

1. A compound of the formula (I)

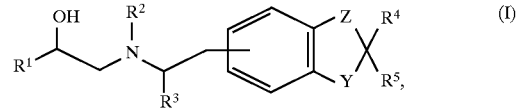

the racemic-enantiomeric mixtures and optical isomers of said compounds or a pharmaceutically acceptable salt or prodrug thereof, wherein $R^1$ is an optionally substituted phenyl, optionally substituted phenoxyalkyl having 1 to 4 carbons in the alkoxy portion, optionally substituted pyridinyl, optionally substituted pyrimidyl, optionally substituted thiazolyl or optionally substituted oxazolyl;

where the optionally substituted moieties of $R^1$ are optionally substituted with one to three substituents, each substituent is independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, $(C_1-C_4)$alkoxycarbonyl, $(C_1-C_4)$thioalkyl, sulfonyl, sulfinyl, amino, —NH—CO—$(CH_2)_a$-(phenyl), —NH—CO—$(C_1-C_{10})$alkyl, —NH—SO$_2$—$(CH_2)_a$-(phenyl) and —NH—SO$_2$—$(C_1-C_{10})$alkyl;

$R^2$ is hydrogen or $(C_1-C_6)$alkyl;

$R^3$ is hydrogen or $(C_1-C_6)$alkyl;

$R^4$ and $R^5$ are each independently selected form the group consisting of hydrogen, —CO$_2$H, —CO$_2R^6$, —CO$_2NR^6R^6$, —CHO, —COR$^6$, —CH$_2$OH, —CH$_2$OCH$_2$CO$_2R^6$ and —CH$_2$OCH$_2$CH$_2$OR$^6$;

$R^6$ for each occurrence is independently selected form the group consisting of hydrogen and $(C_1-C_4)$alkyl;

Y is oxygen or sulfur;

Z is —$(CH_2)_n$—;

n is 1;

$R^7$ is hydrogen, $(C_1-C_{10})$alkyl, $(C_1-C_{10})$alkenyl, —$(CH_2)_a$-(optionally substituted phenyl), —$(CH_2)_a$-(optionally substituted pyridinyl), —CO—$(CH_2)_a$-(optionally substituted phenyl), —CO—$(C_1-C_{10})$alkyl, —SO$_2$—$(CH_2)_a$-(optionally substituted phenyl) or —SO$_2$—$(C_1-C_{10})$alkyl;

where the optionally substituted moieties in the definition of $R^7$ are optionally substituted with one to three substituents, each independently selected form the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, $(C_1-C_4)$alkoxycarbonyl, $(C_1-C_4)$thioalkyl, sulfonyl, sulfinyl, amino, —NH—CO—$(CH_2)_a$-(phenyl), —NH—CO—$(C_1-C_{10})$allyl, —NH—$SO_2$—$(CH_2)_a$-(phenyl) and —NH—$SO_2$—$(C_1-C_{10})$allyl;

a is 0, 1, 2, 3 or 4 provided that $R^4$ and $R^5$ are not both hydrogen at the same time.

2. A compound according to claim 1 where $R^1$ is optionally substituted phenyl; $R^3$ is $(C_1-C_6)$ alkyl; $R^4$ is hydrogen or —$CO_2R^6$; and $R^5$ is —$CO_2R^6$.

3. A compound according to claim 2 where the optionally substituted phenyl of $R^1$ is optionally substituted with a chloro, fluoro, iodo or bromo.

4. A compound according to claim 3 where $R^1$ is

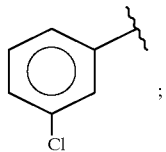

$R^2$ is hydrogen; and the OH in formula I has the

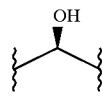

configuration.

5. A compound according to claim 4 where $R^3$ is methyl; Y is O; and $R^4$ and $R^5$ are each —$CO_2CH_2CH_3$.

6. A pharmaceutical composition comprising an effective amount of a compound, or a prodrug thereof, or a pharmaceutically acceptable salt of said compound or prodrug, as defined in claim 1, and a pharmaceutically acceptable carrier.

7. A method of selectively activating a $\beta_3$-adrenergic receptor in a mammal or poultry, comprising administering to a mammal or poultry in need of such activation an effective amount of a compound of formula (I) or a prodrug thereof, or a pharmaceutically acceptable salt of said compound or prodrug, according to claim 1.

8. A method of treating a condition selected from the group consisting of diabetes, hyperglycemia and obesity in a mammal, comprising administering to a mammal in need of such treatment an amount of a compound of formula I, or a prodrug thereof, or a pharmaceutically acceptable salt of said compound or prodrug, according to claim 1, effective in treating such condition.

9. A method of increasing the content of lean meat in animals or poultry comprising administering to an animal or poultry an amount of a compound of formula I, or a prodrug thereof, or a pharmaceutically acceptable salt of said compound or prodrug, according to claim 1, effective in increasing said content.

10. A method for treating prostate disease in a mammal comprising administering to a mammal in need of such treatment an effective amount of a compound of formula I, or a prodrug thereof, or a pharmaceutically acceptable salt of said compound or prodrug according to claim 1.

11. A method of treating intestinal motility disorders in a mammal comprising administering to a mammal in need of such treatment an effective amount of a compound of formula I, or a prodrug thereof, or a pharmaceutically acceptable salt of said compound or prodrug according to claim 1.

12. A method of treating depression in a mammal comprising administering to a mammal in need of such treatment an effective amount of a compound of formula I, or a prodrug thereof, or a pharmaceutically acceptable salt of said compound or prodrug according to claim 1.

13. A method of treating dyslipidemia in a mammal comprising administering to a mammal in need of such treatment an effective amount of a compound of formula I, or a prodrug thereof, or a pharmaceutically acceptable salt of said compound or prodrug according to claim 1.

14. A method for treating airway inflammatory disorders in a mammal comprising administering to a mammal in need of such treatment an effective amount of a compound of formula I, or a prodrug thereof, or a pharmaceutically acceptable salt of said compound or prodrug according to claim 1.

15. A method as defined in claim 14, wherein said airway inflammatory disorder is asthma.

* * * * *